(12) United States Patent
Hecker et al.

(10) Patent No.: US 6,599,741 B1
(45) Date of Patent: Jul. 29, 2003

(54) MODULATING TRANSCRIPTION OF GENES IN VASCULAR CELLS

(75) Inventors: Markus Hecker, Götting (DE); Manfred Lauth, Köln (DE); Andreas H. Wagner, Götting (DE)

(73) Assignee: Avontec GmbH, Gottingen (DE)

( * ) Notice: Subject to any disclaimer, the term of this patent is extended or adjusted under 35 U.S.C. 154(b) by 0 days.

(21) Appl. No.: 09/524,664

(22) Filed: Mar. 13, 2000

(30) Foreign Application Priority Data

Sep. 14, 1999 (DE) .......................................... 299 16 160
Sep. 14, 1999 (JP) ............................................ 11-261035

(51) Int. Cl.$^7$ .......................... C12N 5/00; C12N 15/63; A01K 43/04; A61K 31/07; A61K 49/00
(52) U.S. Cl. ........................ 435/375; 435/455; 435/325; 514/44; 424/9.1; 424/9.2
(58) Field of Search ............................... 424/93.21, 9.1, 424/9.2; 800/3, 8, 9, 11, 13, 18; 435/325, 455, 375; 514/44

(56) References Cited

U.S. PATENT DOCUMENTS

| 5,858,673 A | 1/1999 | Price et al. ..................... 435/6 |
| 5,977,334 A | 11/1999 | Ransohoff et al. ....... 536/23.51 |

FOREIGN PATENT DOCUMENTS

| DE | 2991610 U1 * | 9/1999 |
| EP | 0 856 582 A2 | 8/1998 |
| JP | 06201692 | 7/1994 |
| JP | 07126168 A | 5/1995 |
| JP | 10036272 A | 2/1998 |
| WO | WO 94/20113 | 9/1994 |
| WO | WO 95/01429 | 1/1995 |
| WO | WO 95/02053 | 1/1995 |
| WO | WO 95/11684 | 5/1995 |
| WO | WO 95/11687 | 5/1995 |
| WO | WO 96/12011 | 4/1996 |
| WO | 0 733 370 A1 | 9/1996 |
| WO | WO 98/25967 | 6/1998 |
| WO | WO 98/56806 | 12/1998 |
| WO | WO 99/00488 | 1/1999 |
| WO | WO 99/10486 | 3/1999 |
| WO | WO 99/24574 | 5/1999 |
| WO | WO 99/33999 | 7/1999 |

OTHER PUBLICATIONS

Mann et al. Therapeutic applications of transcription factor decoy oligonucleotides pp. 1071–1075 vol. 106,No. 9 Nov. 2000.*

Redenti et al. Cyclodextrins in oligonycleotide delivery pp. 235–244 2001.*

Nishikawa et al. Nonviral vector in the new millennium: delivery barriers in gene transfer pp. 861–870, May 20, 2001.*

Miller et al.; Targeted vectors for gene therapy, 1995, FASEB J. 9: 190–199.*

Deonarain; Ligand–targeted receptor–mediated vectors for gene delivery, 1998, Exp. Opin. Ther. Parents 8(1): 53–69.*

Verma et al.; Gene therapy–promises, problems and prospects, 1997, Nature vol. 389: 239–242.*

Crystal; Transfer of Genes to Humans: Early Lessons and Obstacles to Success; 1995, Science vol. 270: 404–410.*

Morishita et al.; Oligonucleonucleotide–Based Gene Therapy for Cardiovascular Disease, 1998, Clin. Chem. Lab Med 36:529–534.*

Penning: Hydroxyusteroid dehydrogenase: three dimensional structure and gene regulation, 1996, Journal of Endocrinology 150: S175–S187.*

Salvatore et al.; The Guanosine Monophosphate Reductase Gene is Conserved in Rats and Its Expression . . . Tissue during Cold Exposure, 1998, The Journal of Biological Chemistry, vol.273No. 47: 31092–31096.*

Morishita et al.; Role of AP–1 Complex in Angiotensin 11–Mediated Transforming Growth . . . Using Decoy Approach against AP–1 Binding Site, 1998, Bio. Research Comm. 243: 361–367.*

Uhlmann et al., Studies on the Mechanism of Stabilization of Partially Phosphorothioated Oligonucleotides Against Nucleolytic Degradation, 1997, Nucleic Acid Drug Development 7: 345–350.*

Lauth et al., European Journal of Physiology vol. 437 Supplement; Abstract 017–2 (1999).

Wagner et al., "Transcription Factors AP–1 and C/EBP are involved in the Expression of the Endothelin (ETa) Receptor in Vascular Smooth Muscle Cells," Abstracts of the 78$^{th}$ Annual Meetingk Deutsche Physiologische Gesellschaft, Mar. 14, 1999.

Alam, "Multiple Elements Within the 5' Distal Enhancer of the Mouse Heme Oxygenase–1 Gene Mediate Induction by Heavy Metals," *Chemical Abstracts* 121:172189b (1994).

Beurton et al., "Delineation of the Insulin–Responsive Sequence in the Rat Cytosolic Aspartate Aminotransferase Gene: Binding Sites for Hepatocyte Nuclear Factor–3 and Nuclear Factor I," *Biochem J.* 343:687–695 (1999).

Chandrasekar et al., "Regulation of CCAAT/Enhancer Binding Protein, Interleukin–6, Interleukin–6 Receptor, and gp 130 Expression, During Myocardial Ischemia/Reperfusion," *Chemical Abstracts* 130:323742r (1999).

(List continued on next page.)

*Primary Examiner*—Deborah Crouch
*Assistant Examiner*—Thai-An N. Ton
(74) *Attorney, Agent, or Firm*—Clark & Elbing LLP

(57) ABSTRACT

A method of modulating the transcription of one or more genes in a vascular or cardiac cell, wherein the method comprises a step of contacting the cell with a composition comprising one or more double-stranded nucleic acid(s) capable of sequence-specific binding to the transcription factor AP-1 and/or C/EBP or a related transcription factor.

42 Claims, 11 Drawing Sheets

OTHER PUBLICATIONS

Figure 1A:
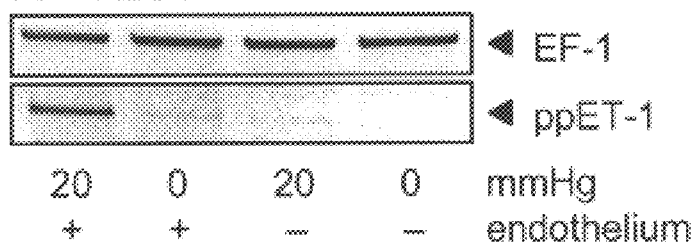
Figure 1A:
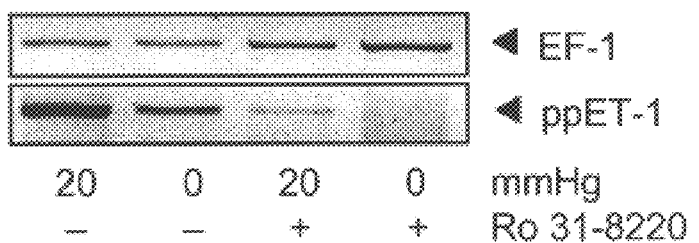
Figure 1A:
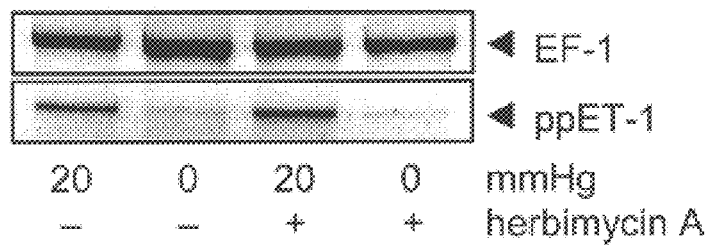
Figure 1B:
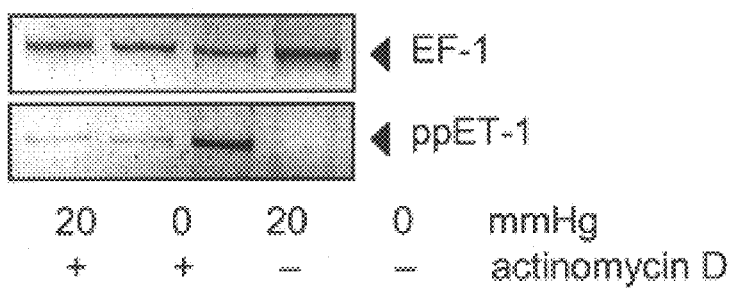
Figure 1B:
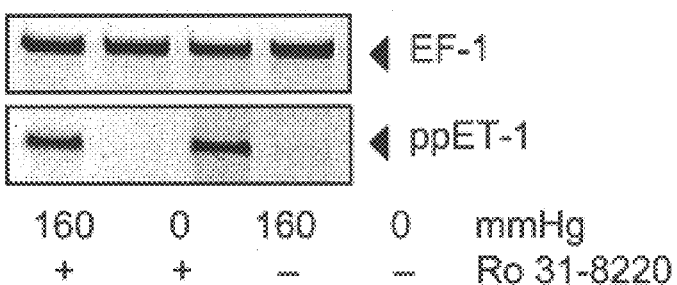
Figure 1B:
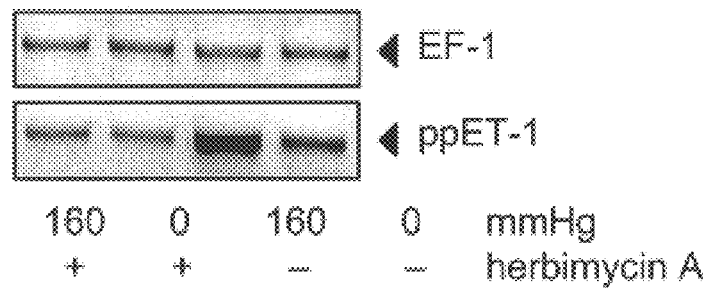

Colangelo et al., "β–Adrenergic Receptor–Induced Activation of Nerve Growth Factor Gene Transcription in Rat Cerebral Cortex Involves CCAAT/Enhancer–Binding Protein δ," *Proc. Natl. Acad. Sci. USA* 95:10920–10925 (1989).

Costa et al., "Site–Directed Mutagenesis of Hepatocyte Nuclear Factor (HNF) Binding Sites in the Mouse Transthyretin (Ttr) Promoter Reveal Synergistic Interactiosn with its Enhancer Regioin," *Chemical Abstracts* 115:176494w (1991).

Eickelberg et al., "Transforming Growth Factor–B1 Induces Interleukin–6 Expression via Activating Protein–1 Consisting of JunD Homodimers in Primary Human Lung Fibroblasts," *Chemical Abstracts* 131:83453x (1999).

Frame et al., "Regulation of AP–1/DNA Complex Formation in vitro," *Chemical Abstracts* 114:180493s (1991).

Guyton et al., "Induction of the Mammalian Stress Response Gene GADD153 by Oxidative Stress: Role of AP–1 Element," *Biochem. J.* 314:547–554 (1996).

Mietus–Snyder et al., "Transcriptional Activation of Scavenger Receptor Expression in Human Smooth Muscle Cells Requires AP–1/c–Jun and C/EBPB; Both AP–1 Binding and JNK Activation are Induced by Phorbol Esters and Oxidative Stress," *Chemical Abstracts* 130:48189y (1999).

Mukaida et al., "Novel Mechanism of Glucocorticoid–Mediated Gene Repression. Nuclear Factor–xB is Target for Glucocorticoid—Mediated Interleukin 8 Gene Repression," *Chemical Abstracts* 120:316132g (1994).

Nishizawa, "Leucine Zipper—A Characteristic Property of a New Category of DNA Binding Proteins," *Chemical Abstracts* 111:210601h (1989).

Nuthall et al., "Analysis of DNase–I–Hypersensitive Sites in the 3' End of the Cystic Fibrosis Transmembrane Conductance Regulator Gene (CFTR)," *Biochem. J.* 341:601–611 (1999).

Ondrey et al., "Constitutive Activation of Transcription Factors NF–xB, AP–1, and NF–IL6 in Human Head and Neck Squamous Cell Carcinoma Cell Lines that Express Pro–Inflammatory and Oro–Angiogneic Cytokines," *Chemical Abstract* 131:335679j (1999).

Ross et al., "A Fat–Specific Enhancer is the Primary Determinant of Gene Expression for Adipocyte P2 in vivo," *Proc. Natl. Acad. Sci. USA* 87:9590–9594 (1990).

Sabatakos et al., "Expression of the Genes Encoding CCAAT–Enhancer Binding Protein isoforms in the Mouse Mammary Gland During Lactation and Involution," *Biochem. J.* 334:205–210 (1998).

Samadani et al., "Identification of a Transthyretin Enhancer Site that Selectively Binds the Hepatocyte Nuclear Factor–3B Isoform," *Chemical Abstracts* 126:55621d (1997).

Stauffer et al., "Characterization of Transcriptional Regulatory Elements in the Pormoter Region of Mring Blood Coagulation Factor VII Gene," *Chemical Abstracts* 128:201628w (1998).

* cited by examiner

D – RbCA

E – PAEC

F – PAEC

Control    AP-1

SEQUENCE LISTING

<160> NUMBER OF SEQ ID NOS: 32

<210> SEQ ID NO 1
<211> LENGTH: 21
<212> TYPE: DNA
<213> ORGANISM: Rattus norwegicus

<400> SEQUENCE: 1
ggagctccag aaacagctgt c                21

<210> SEQ ID NO 2
<211> LENGTH: 24
<212> TYPE: DNA
<213> ORGANISM: Rattus norwegicus

<400> SEQUENCE: 2
ctgctgataa atacacttct ttcc             24

<210> SEQ ID NO 3
<211> LENGTH: 21
<212> TYPE: DNA
<213> ORGANISM: Homo sapiens

<400> SEQUENCE: 3
gacatcacca agggtgtgca g                                              21

<210> SEQ ID NO 4
<211> LENGTH: 20
<212> TYPE: DNA
<213> ORGANISM: Homo sapiens

<400> SEQUENCE: 4
gcggtcagca caatggcata                                                20

<210> SEQ ID NO 5
<211> LENGTH: 21
<212> TYPE: DNA
<213> ORGANISM: Artificial Sequence
<220> FEATURE:
<223> OTHER INFORMATION: consensus binding site for AP-1

<400> SEQUENCE: 5
cgcttgatga ctcagccgga a                                              21

<210> SEQ ID NO 6
<211> LENGTH: 20
<212> TYPE: DNA
<213> ORGANISM: Artificial Sequence
<220> FEATURE:
<223> OTHER INFORMATION: consensus binding site for C/EBP

<400> SEQUENCE: 6
tgcagattgc gcaatctgca                                                20

<210> SEQ ID NO 7
<211> LENGTH: 20
<212> TYPE: DNA
<213> ORGANISM: Artificial Sequence
<220> FEATURE:
<223> OTHER INFORMATION: mutated consensus binding site for C/EBP

<400> SEQUENCE: 7
tgcagagact agtctctgca                                                20

<210> SEQ ID NO 8
<211> LENGTH: 27
<212> TYPE: DNA
<213> ORGANISM: consensus binding site for GATA-2

<400> SEQUENCE: 8
cacttgataa cagaaagtga taactct                                        27

<210> SEQ ID NO 9
<211> LENGTH: 21
<212> TYPE: DNA
<213> ORGANISM: Artificial Sequence
<220> FEATURE:
<223> OTHER INFORMATION: designed AP-1

<400> SEQUENCE: 9
ctgttggtga ctaataacac a                                              21

<210> SEQ ID NO 10
<211> LENGTH: 21
<212> TYPE: DNA
<213> ORGANISM: Artificial Sequence
<220> FEATURE:
<223> OTHER INFORMATION: designed AP-1

<400> SEQUENCE: 10

-continued ctgtgggtga ctaatcacac a                            21

<210> SEQ ID NO 11
<211> LENGTH: 15
<212> TYPE: DNA
<213> ORGANISM: Artificial Sequence
<220> FEATURE:
<223> OTHER INFORMATION: designed AP-1

<400> SEQUENCE: 11
gtgctgactc agcac                                   15

<210> SEQ ID NO 12
<211> LENGTH: 17
<212> TYPE: DNA
<213> ORGANISM: Artificial Sequence
<220> FEATURE:
<223> OTHER INFORMATION: designed AP-1

<400> SEQUENCE: 12
cgcttagtga ctaagcg                                 17

<210> SEQ ID NO 13
<211> LENGTH: 17
<212> TYPE: DNA
<213> ORGANISM: Artificial Sequence
<220> FEATURE:
<223> OTHER INFORMATION: designed AP-1

<400> SEQUENCE: 13
tgtgctgact cagcaca                                 17

<210> SEQ ID NO 14
<211> LENGTH: 19
<212> TYPE: DNA
<213> ORGANISM: Artificial Sequence
<220> FEATURE:
<223> OTHER INFORMATION: designed AP-1

<400> SEQUENCE: 14
ttgtgctgac tcagcacaa                               19

<210> SEQ ID NO 15
<211> LENGTH: 19
<212> TYPE: DNA
<213> ORGANISM: Artificial Sequence
<220> FEATURE:
<223> OTHER INFORMATION: designed AP-1

<400> SEQUENCE: 15
tcgcttagtg actaagcga                               19

<210> SEQ ID NO 16
<211> LENGTH: 20
<212> TYPE: DNA
<213> ORGANISM: Artificial Sequence
<220> FEATURE:
<223> OTHER INFORMATION: designed AP-1

<400> SEQUENCE: 16
tgctgactca tgagtcagca                              20

<210> SEQ ID NO 17
<211> LENGTH: 20
<212> TYPE: DNA

```
<213> ORGANISM: Artificial Sequence
<220> FEATURE:
<223> OTHER INFORMATION: designed AP-1

<400> SEQUENCE: 17
tgctgactaa ttagtcagca                                              20

<210> SEQ ID NO 18
<211> LENGTH: 21
<212> TYPE: DNA
<213> ORGANISM: Artificial Sequence
<220> FEATURE:
<223> OTHER INFORMATION: designed AP-1

<400> SEQUENCE: 18
gtcgcttagt gactaagcga c                                            21

<210> SEQ ID NO 19
<211> LENGTH: 21
<212> TYPE: DNA
<213> ORGANISM: Artificial Sequence
<220> FEATURE:
<223> OTHER INFORMATION: designed AP-1

<400> SEQUENCE: 19
cttgtgctga ctcagcacaa g                                            21

<210> SEQ ID NO 20
<211> LENGTH: 22
<212> TYPE: DNA
<213> ORGANISM: Artificial Sequence
<220> FEATURE:
<223> OTHER INFORMATION: designed AP-1

<400> SEQUENCE: 20
ttgctgactc atgagtcagc aa                                           22

<210> SEQ ID NO 21
<211> LENGTH: 20
<212> TYPE: DNA
<213> ORGANISM: Artificial Sequence
<220> FEATURE:
<223> OTHER INFORMATION: designed C/EBP

<400> SEQUENCE: 21
gcttgtgcgg gaataaatag                                              20

<210> SEQ ID NO 22
<211> LENGTH: 20
<212> TYPE: DNA
<213> ORGANISM: rat PPET-1

<400> SEQUENCE: 22
aggaataatg gaatgccctg                                              20

<210> SEQ ID NO 23
<211> LENGTH: 16
<212> TYPE: DNA
<213> ORGANISM: Artificial Sequence
<220> FEATURE:
<223> OTHER INFORMATION: designed C/EBP

<400> SEQUENCE: 23
gacattgcgc aatgtc                                                  16
```

```
<210> SEQ ID NO 24
<211> LENGTH: 16
<212> TYPE: DNA
<213> ORGANISM: Artificial Sequence
<220> FEATURE:
<223> OTHER INFORMATION: designed C/EBP

<400> SEQUENCE: 24
agcattggcc aatgct                                                    16

<210> SEQ ID NO 25
<211> LENGTH: 18
<212> TYPE: DNA
<213> ORGANISM: Artificial Sequence
<220> FEATURE:
<223> OTHER INFORMATION: designed C/EBP

<400> SEQUENCE: 25
cgacattgcg caatgtcg                                                  18

<210> SEQ ID NO 26
<211> LENGTH: 18
<212> TYPE: DNA
<213> ORGANISM: Artificial Sequence
<220> FEATURE:
<223> OTHER INFORMATION: designed C/EBP

<400> SEQUENCE: 26
aggcattggc caatgcct                                                  18

<210> SEQ ID NO 27
<211> LENGTH: 20
<212> TYPE: DNA
<213> ORGANISM: Artificial Sequence
<220> FEATURE:
<223> OTHER INFORMATION: designed C/EBP

<400> SEQUENCE: 27
acgacattgc gcaatgtcgt                                                20

<210> SEQ ID NO 28
<211> LENGTH: 20
<212> TYPE: DNA
<213> ORGANISM: Artificial Sequence
<220> FEATURE:
<223> OTHER INFORMATION: designed C/EBP

<400> SEQUENCE: 28
taggcattgg ccaatgccta                                                20

<210> SEQ ID NO 29
<211> LENGTH: 22
<212> TYPE: DNA
<213> ORGANISM: Artificial Sequence
<220> FEATURE:
<223> OTHER INFORMATION: designed C/EBP

<400> SEQUENCE: 29
ctgttgcgca attgcgcaac ag                                             22

<210> SEQ ID NO 30
<211> LENGTH: 22
<212> TYPE: DNA
<213> ORGANISM: Artificial Sequence
<220> FEATURE:
<223> OTHER INFORMATION: designed C/EBP
```

```
<400> SEQUENCE: 30
gacttgcgca attgcgcaag tc                                            22

<210> SEQ ID NO 31
<211> LENGTH: 21
<212> TYPE: DNA
<213> ORGANISM: Artificial Sequence
<220> FEATURE:
<223> OTHER INFORMATION: designed AP-1

<400> SEQUENCE: 31
cgcttgatga ctcagccgga a                                             21

<210> SEQ ID NO 32
<211> LENGTH: 17
<212> TYPE: DNA
<213> ORGANISM: Artificial Sequence
<220> FEATURE:
<223> OTHER INFORMATION: designed C/EBP

<400> SEQUENCE: 32
tgcagattgc gcaattg                                                  17
```

MODULATING TRANSCRIPTION OF GENES IN VASCULAR CELLS

CROSS REFERENCE TO RELATED APPLICATIONS

This application claims benefit from German application DE 299 16 160.9 and Japanese application JP 261035/99, both of which were filed Sep. 14, 1999.

A method of modulating the transcription of one or more genes in a vascular or cardiac cell, wherein the method comprises a step of contacting said cell with a composition comprising one or more double-stranded nucleic acid(s) capable of sequence-specific binding to the transcription factor AP-1 and/or C/EBP or a related transcription factor.

Coronary Heart Disease (CHD) is the leading cause of death in industrialized nations. The last decades have seen an increasing use of aortocoronary venous bypass surgery as well as percutanous transluminal coronary angioplasty (PTCA) for the treatment of Coronary Heart Disease which substantially increased survival rates as well as quality of life of heart patients.

Although these methods have been well established for decades, they still have a high probability of relapse or of complete occlusion of the treated vessel (30-50%) and often this complication is already apparent within a few months after surgery. This represents a substantial medical problem and is also an economical burden for the health systems of the industrialized world.

One of the major reasons for complications observed with PTCA as well as coronary bypass surgery seems to be the induction of migration and proliferation of cells of the vessel wall. This untimely and unwanted proliferation of vascular tissue results in remodeling processes that eventually cause relapses and obstruction of surgically treated vessels.

To prevent postoperative relapse or occlusion of a treated vessel segment, a recently employed strategy is the implantation of stents, tubular structures that are designed to maintain the postoperative shape and diameter of a vessel after PTCA. But this method is also complicated by the development of in-stent restenosis as a result of excessive proliferation and migration of smooth muscle cells due to mechanical strain on the vessel wall. Additionally, several clinical studies using a variety of adjuvant medication therapies where not able to efficiently suppress these side effects of surgical intervention.

Consequence of therapeutic failure is the (re-)occlusion of myocardial blood vessels, which leads to ischemic episodes and, in severe cases, to myocardial infarction (MI). This is accompanied by massive death of cardiomyocytes in areas of the heart muscle with insufficient oxygen supply, consequently leaving incontractile scar tissue. Thus, re-opening of vessels, induction of vessel growth in ischemic areas of the heart muscle and/or induction of proliferation of cardiomyocytes could present a possible therapeutic approach for treatment of MI.

Most cells in the body are in the $G_0$-phase of the cell cycle which is called the quiescent state. Almost all quiescent body cells still have the ability to proliferate and can be induced to reenter the cell cycle by a number of stimuli the most important being growth factors and injury. Proliferation as well as remodeling processes are primarily regulated on the level of transcription. The physical stress of, for instance, coronary angioplasty and stent implantation will therefore lead to induction of a number of genes most importantly cyclins, cell cycle specific phosphatases and cell cycle specific transcription factors like for instance cyclin E, cyclin A, cyclin B, cdc25C, cdc25A, E2F-family members as well as a number of metabolically important genes or genes that are involved in the doubling of DNA like for instance PCNA, histones and dhfr. While those factors are newly synthesized upon entry into the cell cycle many transcription factors involved in the first steps of proliferation, the so called immediate-early genes, are already present in the cell and are activated upon a given stimulus, a well known member of this class is AP-1.

AP-1 is a heterodimeric transcription factor consisting of c-Jun and c-Fos protein (Curran and Franza (1988) Cell 55, 395) that interact via a leucine zipper motif with each other. Unlike c-Jun, that is able to homodimerize and bind DNA on its own, c-Fos is dependent on interaction with c-Jun for sequence specific binding to DNA. Both proteins are members of a larger family of proteins that include for instance JunB and JunD (Jun related) as well as for instance Fral and FosB (Fos related) (Curran and Vogt (1992) in Transcriptional Regulation, 797 (McKnight and Yamamoto) Cold Spring Harbor Laboratory Press). AP-1 is able to bind to a consensus sequence TGACTCA motif but many variations of this sequence can be avidly bound by various homo- and heterodimers of the AP-1 family members (Franza et al. (1988) Science 239, 1150; Rauscher et al. (1988) Genes Dev. 2, 1687; Risse et al. (1989) EMBO J. 8, 3825; Yang-Yen et al. (1990) New Biol 2, 351).

Although coexpression of Fos and Jun can lead to dramatic synergistic activation of AP-1-dependent transcription (Chiu et al. (1988) Cell 54, 541) a substantial degree of experimental variability has been encountered depending on the cell type used. Therefore, it is likely that the activities of Fos and Jun are influenced by other proteins that may be expressed in a cell type-specific manner (Baichwal and Tjian (1990) Cell 63, 815) and that in each cell type, the presence of resident or inducible transcription factors may influence both the selection of gene targets and the transcriptional effect of Fos-Jun family hetero- and homodimers. Consistent with the promoter and cell type specificity of AP-1, Fos was shown not to activate but rather to repress transcription of the c-fos promoter (Sassone-Corsi (1988) Cell 54, 553; Lucibello et al. (1989) Cell 59, 999). Consequently, it is not possible to predict what effect AP-I might have on a specific promoter in a given cell type.

A method to specifically interfere with transcriptional activation by a specific transcription factor is disclosed in WO 95/11687. It teaches that it is possible to interfere with the activating function of a transcription factor by treating a cell with a double-stranded DNA molecule, termed cis-element decoy, carrying a binding site for that specific transcription factor. Exogenous supply of a high number of transcription factor binding sites to a cell, preferentially in much higher numbers than present in endogenous promoters in the genome, creates a situation where the majority of a given transcription factor will bind specifically to the respective cis-element decoy rather than to its endogenous target genes. This approach for inhibiting the binding of a transcription factor to its endogenous binding site is also referred to as squelching. Squelching of transcription using DNA decoys has been successfully employed to inhibit proliferation of cells using DNA fragments that specifically target the transcription factor E2F (Morishita et al. (1995) Proc. Natl. Acad. Sci. U.S.A. 92, 5855).

It is speculated by extrapolating the current results of the Human Genome Project that about 50% of all human genes are transcription factors. The complexity and diversity of organisms is known to be in large part caused by the restriction of expression of certain transcription factors to specific cell types and/or to specific stages of development. A transcription factor that has a positive effect on proliferation in one cell type might have an opposite effect in another cell type or in another species. Thus, the effect of treatment with a given transcription factor decoy may vary not only between species, but also between various tissues, for example veins and arteries, and between cell types in a given tissue, for example endothelial cells and smooth muscle cells of a vessel wall, within one organism.

Therefore, one of the objectives of the present invention is the targeting of transcription factors that modulate transcription in vascular cells, including endothelial and smooth muscle cells, or cardiac cells and which thus would be appropriate targets for squelching by double-stranded nucleic acids having a sequence specific for binding the transcription factor. Preferred transcription factor targets are transcriptions factors that are directly or indirectly involved in inducing proliferation and/or remodeling of vascular tissue and/or myocardial tissue.

Surprisingly, it was found that the activation of the endothelin-1 (ET-1) gene is mediated by AP-1 in venous endothelial cells. This activation was triggered by application of excessive mechanical stress. The ET-1 peptide that is produced in response to this stimulus is highly potent in vasoconstriction and promotion of cellular proliferation. Release of ET-1 has been correlated with excess growth of smooth muscle cells as well as remodeling. Subsequently it was possible to show that the activation of the ET-1 gene in endothelial cells could be blocked by introducing double-stranded DNA bearing the binding site for AP-1.

Accordingly, a method of the present invention is the modulation of transcription of at least one gene in an endothelial or cardiac cell, wherein the method comprises the step of contacting said cell with a composition comprising one or more double-stranded nucleic acid(s) capable of sequence-specific binding to the transcription factor AP-1 or a related transcription factor. This method will be used in particular on endothelial cells that are part of a vessel or a vascular graft. Typically the method can be used on the vessel in vivo or on a vascular graft in vivo before or after implantation or ex vivo prior to implantation. Preferentially, the cardiac cell is a cardiomyocyte or a fibroblast.

Another unexpected result of the present invention was the discovery that CCAAT/enhancer-binding protein (C/EBP) is involved in the activation of ET-1 in endothelial cells of the Aorta carotis after applying mechanical stress. Consistent with the above described differential effects of transcription factors in different tissues AP-1 was not involved in activation of the ET-1 gene in this cell type. When C/EBP specific double-stranded nucleic acids were introduced into the endothelial cells of the Aorta carotis, activation of the ET-1 gene could be blocked.

C/EBPs comprise a family of transcription factors that are critical for normal cellular differentiation and function in a variety of tissues (reviewed in Lekstrom-Himes and Xanthopoulos (1996) J. Biol. Chem 44, 28645). There are at least six members of the C/EBP family (Cao et al. (1991) Genes Dev. 5, 1538) which only bind to DNA upon dimerization. C/EBP family members have been studied in particular for their role in the liver and are known to be involved in the acute phase response after liver damage (reviewed in Fey et al. (1990) in Progress in Liver Diseases (Popper and Schaffner) Vol. 9, 89, W.B. Saunders Co., Philadelphia). C/EBP family members have also been shown to play a major role in inflammation response and C/EBP binding motifs have been recognized in promoters of inflammatory cytokines like interleukin-6 (IL-6), IL-1β and tumor necrosis factor α (TNFα) as well as other cytokines like IL-8 and IL-12 (Matsusaka et al. 1993) Proc. Natl. Acad. Sci. 90, 10193; Plevy et al. (1997) Mol. Cell Biol. 17, 4572). The involvement of C/EBP in transcriptional activation of ET-1, a factor that is known to promote growth and remodeling of vascular tissue points toward another suitable transcription factor target in vascular cells.

Accordingly, another method of the present invention is the modulation of transcription of one or more genes in a vascular or cardiac cell, wherein the method comprises the step of contacting said cell with a composition comprising one or more double-stranded nucleic acid(s) capable of sequence-specific binding to the transcription factor C/EBP or related transcription factors.

It is known that individual transcription factors can often activate a promoter to a certain degree on their own but that full activation of that promoter depends on the synergistic activation by two or more transcription factors (Sauer et al. (1995) Science 270, 1783). Consequently, to achieve a stronger modulation of a promoter than with a double-stranded nucleic acid targeted against a single transcription factor it is also envisioned that the method of the present invention is carried out with a composition comprising one or more sequences that specifically binds C/EBP and additionally comprises one or more double-stranded nucleic acids capable of sequence-specific binding to the transcription factor AP-1. This combination will, for example, allow a stronger modulation of transcription of promoters that contain both AP-1 and C/EBP binding sites or it will allow to affect at the same time two or more promoters independently.

When using the method of the present invention on vascular cells, the preferential targets are smooth muscle cells (SMC) or endothelial cells while for cardiac cells, the preferred targets are cardiomyocytes or fibroblasts. These cells are, for example, treated directly in the animal or human in the vessel in situ or they can be part of an autologous or heterologous vascular graft. These grafts, for instance arterial or venous bypass grafts, can be treated prior to implantation by ex vivo application of the method of the present invention or after implantation by in vivo application of the method. In a preferred embodiment the treated vessel is a coronary or peripheral artery or an arterio-venous fistula (e.g. Brescia-Cimino fistula) and the vascular graft is a arterial or venous bypass graft or a biologic or prosthetic arterio-venous shunt.

To prevent, for instance, occlusion of vessels caused by a surgical procedure or by a pathological process it is intended to specifically modulate expression of genes that are involved in proliferation or migration of vascular cells. This modulation can be a direct effect on the promoter of said gene by squelching the binding of AP-1, C/EBP or a related protein or it can be an indirect effect by interfering with the regulation of a transcription factor that itself modulates a gene involved in proliferation or migration of vascular cells. Genes that are involved in proliferation or migration include genes coding for proteins that are active within a cell like, for instance, cyclins, cyclin dependent kinases, inhibitors of apoptosis and genes coding for proteins that are secreted and are thus active outside the cell like, for instance, metalloproteinases, collagenase or growth factors. In particular growth factors that are secreted by one vascular cell can stimulate the growth and migration of a number of other vascular cells. Therefore, the modulation of genes that exert effects outside the targeted cell are of particular importance for the present invention.

The sequence of a nucleic acid that is used for inhibiting the binding of transcription factors AP-1, C/EBP or a related transcription factor is, for instance, a consensus sequence derived from the sequence of AP-1 or C/EBP sites in many promoters such as 5'-CGCTTGATGACTCAGCCGGAA-3' (SEQ ID NO: 5) (for AP-1) or 5'-TGCAGATT GCGCAATTG-3' (SEQ ID NO: 32) (for C/EBP) or it will be identical to the AP-1 or C/EBP site in the particular promoter or enhancer that is targeted for transcriptional regulation. As pointed out above both AP-1 and C/EBP are members of families of closely related transcription factors that are able to hetero- or homodimerize (Roman et al (1990) Genes Dev. 4, 1404; Cao et al (1991) Genes Dev. 5, 1538). There is large number of possible heterodimers that are likely to recognize different bona fide AP-1 or C/EBP binding sites with different affinities. Thus, the slightly divergent AP-1 or C/EBP binding sites present in different promoters might preferentially be bound by only certain hetero- or homodimers of AP-1, C/EBP or related transcription factors (Akira et al. (1990) EMBO J. 9, 1897, Risse et al. (1989) supra). Therefore, using promoter-specific designed nucleic acids may allow a targeted squelching of the transcription factors that are involved in regulating that particular promoter. If a promoter contains more than one version of an AP-1 and/or C/EBP binding site, which is often the case, nucleic acids representing the sequence of all those binding sites may be used simultaneously. Similarly, one or more double-stranded nucleic acids containing slightly different versions of the consensus transcription factor binding site can also be used simultaneously.

The affinity of binding of nucleic acid sequences to AP-1, C/EBP or related transcription factors can be determined using the electrophoretic mobility shift assay (EMSA) (Sambrook et al. (1989) Molecular cloning. Cold Spring Harbor Laboratory Press; Krzesz et al. (1999) FEBS Lett. 453, 191). This assay is suitable for the quality control of nucleic acids that are intended for use in the method of the present invention or for determination of the optimal length of a binding site. It is also useful for the identification of other sequences that are bound by AP-1, C/EBP or related transcription factors. Most suitable for such an EMSA intended to isolate new binding sequences are purified or recombinantly expressed versions of AP-1, C/EBP or related transcription factors that are employed in several alternating rounds of PCR amplification and selection by EMSA (Thiesen and Bach (1990) Nucleic Acids Res. 18, 3203)

As pointed out above genes that contain binding sites for AP-1 and/or C/EBP or related transcription factors are suitable targets for the method of the present invention as well as genes that are indirectly affected. Genes that code for proteins involved in proliferation and/or remodeling of vascular tissue as well as in other pathologic processes are the endothelin gene family, the macrophage chemotactic protein (MCP) gene family and the nitric oxid synthase (NOS) gene family, examples of such genes with particular importance for vascular cells are the prepro-endothelin-1 gene, the MCP-1 gene and the inducible NOS gene.

Genes that are known to contain AP-1 binding sites in their promoter or enhancer region and that are thus putative targets for specific squelching by the method of the present invention are, for instance, the prepro-endothelin-1 gene, the endothelin receptor B gene, the inducible NOS (iNOS) gene, the E-selectin gene, the monocyte chemotactic protein-1 (MCP-1) gene, the intercellular adhesion molecule-1 (ICAM-1) gene and the interleukin-8 (Il-8) gene.

Genes that are known to contain C/EBP binding sites in their promoter or enhancer region and that are thus putative targets for specific squelching by the method of the present invention are, for instance: prepro-endothelin-1 gene, the endothelin receptor B gene, the iNOS gene, the E-selectin gene, the intercellular adhesion molecule-1 (ICAM- 1) gene, the Il–8 gene and the Il–6 gene.

The method of the present invention modulates the transcription of a gene or genes in such a way that the gene or genes are activated. Activation means within the present invention that the transcription rate is increased compared to cells that were not treated with a composition comprising a double-stranded nuclei acid. Such an increase can be detected, for instance by northern blot (Sambrook et al. (1989) supra) or RT-PCR (Sambrook et al. (1989) supra). Typically, such an increase would be at least a 2-fold, more preferred at least a 5-fold, at least a 20-fold and most preferred at least a 100-fold increase. Activation will for instance be achieved, if AP-1 and/or C/EBP or a related transcription factor functions as a transcriptional repressor on a particular gene and thus squelching of the repressor leads to loss of repression. Loss of repression can not necessarily be equated with activation but it is known for several promoters that loss of the binding of a repressor can be sufficient for activation (Zwicker et al. (1995) EMBO J. 14, 4514).

The method of the present invention also modulates the transcription of a gene or genes in such a way that the gene or genes lose(s) activation or are repressed. Loss of activation repression means within the present invention that the transcription rate is decreased compared to cells that were not treated with a composition comprising a double-stranded nuclei acid. Such a decrease can be detected, for instance by northern blot (Sambrook et al. (1989) supra) or RT-PCR (Sambrook et al. (1989) supra). Typically, such a decrease would be at least a 2-fold, more preferred at least a 5-fold, at least a 20-fold and most preferred at least a 100-fold decrease. Loss of activation or repression will for instance be achieved, if AP-1 and/or C/EBP or a related transcription factor functions as a transcriptional activator on a particular gene and thus squelching of the activator leads to loss of activation or repression.

In another embodiment of the present invention the modulation leads at the same time to activation of a gene or genes while another gene or genes lose activation or are repressed. The differential effect on individual genes can be easily monitored, for instance by northern blot (Sambrook et al. (1989) supra) or RT-PCR (Sambrook et al. (1989) supra) as well as with DNA chip array technology (U.S. Pat. No. 5,837,466).

The double-stranded nucleic acid used in the method of the present invention comprises in a preferred embodiment one or more copies of a sequence that specifically binds AP-1 and/or C/EBP or a related transcription factor. Synthetic nucleic acids are typically at most 100 bp in length and thus can comprise one or up to 10 complete transcription factor binding sites depending on the length of the specific transcription factor recognition site that is chosen. Nucleic acids that are amplified through enzymatic methods, for instance, PCR or propagated in an appropriate prokaryotic or eukaryotic host contain at least about 10 copies, preferably at least about 30 copies, at least about 100 copies or at least about 300 copies of the respective transcription factor binding site.

The double-stranded nucleic acid used in the method of the present invention is, for example, a vector or an oligonucleotide. In a preferred embodiment the vector is a plasmid vector and in particular a plasmid vector that is able to replicate autosomally (Wohlgemuth et al. (1996) Gene Ther. 6, 503–12), thereby increasing the stability of the introduced double-stranded nucleic acid. The length of the double-stranded oligonucleotide will typically be chosen to be between about 10–100 bp, preferentially between about 20–60 bp and most preferred between 30–40 bp.

Oligonucleotides are usually subject to rapid degradation by endo- and exonucleases, in particular DNases and RNases in the cell. Therefore, to maintain a high concentration of the nucleic acid in the cell for an extended period of time the nucleic acid is modified to stabilize it against degradation. Typically such a stabilization can be obtained through the introduction of one or more modified internucleotide phosphate residues or by introduction of one or more "dephospho" internucleotides.

A successfully stabilized nucleic acid will not necessarily contain such a internucleotide at every nucleotide position. It is envisioned that different modifications are introduced into the nucleic acid and that the resulting double-stranded nucleic acids are tested for sequence specific binding to AP-1, C/EBP or related proteins using the routine EMSA assay. This assay allows the determination of the binding constant of the nucleic acid and thus the determination whether the affinity has been changed by the modification. Modified nucleic acids that show sufficient binding can be selected, wherein sufficient binding means at least about 50%, or at least about 75% and most preferred about 100% of the binding of the unmodified nucleic acid.

A nucleic acid that still shows sufficient binding will be tested whether it is more stable in the cell than unmodified nucleic acid. The employed in vitro assay system uses the method of the present invention to introduce the modified nucleic acid into a cell. Subsequently, transfected cells can be removed at different time points and can be analyzed by northern blot (Sambrook et al. (1989) supra), southern blot (Sambrook et al. (1989) supra), PCR (Sambrook et al. (1989) supra), RT-PCR (Sambrook et al. (1989) supra) or DNA chip array (U.S. Pat. No. 5,837,466) techniques for the amount of remaining nucleic acid. A successfully modified nucleic acid will have a half life in the cell of at least about 48 h, more preferred of at least about 4 d, most preferred of at least about 14 d.

Suitable modified internucleotides are reviewed in Uhlmann and Peyman ((1990) Chem. Rev. 90, 544). Modified internucleotide phospate residues and/or "dephospho" bridges that can be comprised in an nucleic acid employed in a method of the present invention are, for example, methylphosphonate, phosphorothioate, phosphorodithioate, phosphor-amidates, phosphate esters, while "dephospo" internucleotide analogues contain, for example, siloxane bridges, carbonate bridges, carboxymethyl ester bridges, acetamidate bridges and/or thioether bridges. It is also envisioned that this type of modification will improve the shelf live of a composition that is intended for use in a method of the present invention.

Another embodiment of the invention is the stabilization of nucleic acids by introducing structural features into the nucleic acids that increase the half life of the nucleic acid. U.S. Pat. No. 5,683,985 discloses such structures, including hairpins and dumbbell DNA. Envisioned is also the simultaneous introduction of modified internucleotide phospate residues and/or "dephospho" bridges together with said structures. The resulting nucleic acids can be tested in an assay system as described above for binding and stability in the cell.

The composition comprising double-stranded nucleic acids is brought into contact with vascular cells or cardiac cells. The intention of this contacting is the transfer of double-stranded nucleic acids that bind AP-1 and/or C/EBP or a related transcription factor into the cell and in particular into the nucleus of the cell. Therefore, nucleic acid modifications and/or additives or auxiliaries that are known to increase the penetration through membranes are also intended to be used within the present invention (Uhlmann and Peyman (1990) Chem. Rev. 90, 544).

A composition according to the invention comprises in one preferred embodiment essentially only nucleic acid and buffer. This method employs high concentrations of the double-stranded nucleic acid to allow efficient uptake of the nucleic acid into the cell and ultimately high concentrations of the nucleic acid in the nucleus. A suitable concentration of nucleic acids is at least 1 $\mu$M, more preferentially 10 $\mu$M and most preferred 50 $\mu$M to which one or more suitable buffers are added. One example of such buffers is Tyrode solution containing 144.3 mmol/l Na$^+$, 4.0 mmol/l K$^+$, 138.6 mmol/l Cl$^-$, 1.7 mmol/l Ca$^{2+}$, 1.0 mmol/l Mg$^{2+}$, 0.4 mmol/l HPO$_4^{2-}$, 19.9 mmol/l HCO$_3^-$, 10.0 mmol/l D-glucose.

In another embodiment of the invention the composition further comprises at least one additive and/or auxiliary substance. Additives and/or auxiliary substances like lipids, cationic lipids, polymers, nucleic acid aptamers, peptides and proteins are intended, for example, to increase the transfer of nucleic acids into cells, to target the composition to only a subset of cells, to prevent degradation of the nucleic acid inside the cell, facilitate storage of the nucleic acid composition prior to application and/or improve transfer into the nucleus of the cell.

Auxiliary substances that increase the transfer of nucleic acids into the cells can be, for example, proteins or peptides, which are bound to a DNA or synthetic peptid-DNA molecules that facilitate the transport of the nucleic acid into the nucleus of the cell (Schwartz et al. (1999) Gene Therapy 6, 282; Brandén et al. (1999) Nature Biotechnology 17, 784). Auxiliary substances also include molecules that facilitate release of nucleic acids into the cytoplasm of a cell (Planck et al. (1994) J. Biol. Chem. 269, 12918; Kichler et al. (1997) Bioconjug. Chem. 8, 213) or, for example, liposomes (Uhlmann and Peyman (1990) supra).

To target the composition specifically to a subset of cells the auxiliary substance can be selected to recognize a protein of the target cell, preferentially a protein or protein domain that is exposed on the outside of the cell. The specific targeting can also be described as specific recognition of cells. There are at least two classes of suitable auxiliary substances to achieve this recognition. One class of auxiliary substances comprises antibodies or antibody fragments that recognize preferentially proteins or protein domains that are located on the extracellular side of the cell membrane. Antibodies directed against such membrane structures of endothelial cells were described, for example by Burrows et al. ((1994) Pharmac. Ther. 64, 155), Hughes et al. ((1989) Cancer Res. 49, 6214) and Maruyama et al. ((1990) Proc. Nat. Aca. Sci. 87, 5744). Alternatively, antibodies that are intended to be used are directed against membrane structures of smooth muscle cells, such as, for example:

the antibody 10F3 (Printseva et al. (1987) Exp. Cell Res. 169, 85)

antibodies against actin (Desmoliere et al. (1988) Comptes Reudus des Seances de la Soc. de Biol et de ses Filiales 182, 391)

antibodies against angiotensin II receptors (Butcher et al. (1993) BBRA 196, 1280 antibodies against receptors for growth factors (Reviews in Mendelsohn (1988) Prog. All. 45, 147; Sato et al. (1989) J. Nat. Canc. Inst. 81, 1600; Hynes et al. (1994) BBA 1198, 165)

or antibodies directed for example, against

EGF receptor (Fan et al. (1993) Cancer Res. 53, 4322; Bender et al. (1992) Cancer Res. 52, 121; Aboud-Pirak et al. (1988) J. Nat. Cancer Inst. 80, 1605) p1 PDGF receptor (Yu et al. (1994) J. Biol. Chem. 269, 10668; Kelly et al. (1991) 266, 8987)

FGF receptor (Vanhalteswaran et al. (1991) J. Cell Biol. 115, 418; Zhan et al. (1994) J. Biol. Chem. 269, 20221).

The other class of auxiliary substances are ligands that bind with high affinity to cell surface receptors. Such ligands can be the natural ligand of said receptor or a modified ligand with an even higher affinity. Typically such a ligand is a peptide known to bind to a given membrane receptor. Additionally, it is possible to isolated novel peptide ligands using the receptor of interest in screening a combinatorial peptide library (Lu, Z. et al. (1995) Biotechnol. 13, 366; U.S. Pat. No. 5,635,182; Koivunen, E. et al. (1999) J. Nucl. Med. 40, 883).

Membrane receptors expressed on endothelial cells, that can be targeted by said ligands include for example PDGF, bFGF, VEGF and TGFβ (Pusztain et al. (1993) J. Pathol. 169, 191). In addition the ligand also includes adhesion molecules which bind to proliferating/migrating endothelial cells. Adhesion molecules of this type, such as, for example, SLex, LFA-1, MAC-1, LECAM-1 or VLA-4, have already been described (reviews in Augstein-Voss et al. (1992) J. Cell Biol. 119, 483; Pauli et al. (1990) Cancer Metast. Rev. 9, 175; Honn et al. (1992) Cancer Metast. Rev. 11, 353). But the ligand is not limited to a peptide ligand it can also be, for example, a nucleic acid-aptamer specificly recognizing the cell surface of a target cell (Hicke, B. J. et al. (1996) J. Clin. Invest. 98, 2688).

Membrane receptors that are expressed on smooth muscle cells that can be targeted by said ligands include for example PDGF, EGF, TGFα, FGF, endothelin A and TGFβ (reviewed in Pusztain et al. (1993) J. Pathol. 169, 191; Harris (1991) Current Opin. Biotechnol. 2, 260).

Additives that stabilize the nucleic acid within the cell are, for example, nucleic acid-condensing substances like cationic polymers, poly-L-lysin or polyethylenimin.

The composition used in the method of the present invention is preferentially applied locally through injection, catheter, trocars, projectiles, pluronic gels, sustained drug release polymers, coated stents or any other device which provides for local access. An ex vivo application of the composition used in the method of the present invention also provides for local access.

Another embodiment of the present invention is a method of treating vascular diseases, preferentially vascular proliferative disorders, wherein the method comprises the step of contacting vascular cells with a composition as described above in an amount sufficient to modulate the transcription of one or more genes. Diseases that are envisioned to be treated with this method include, for example, restenosis, intimal hyperplasia of arterial or venous bypass grafts, graft vasculopathy and hypertrophy. It is also envisioned that this method can be employed as an adjuvant therapy for treatments frequently used in vascular diseases like for example, PTCAs, PTAs, bypass operations or application of arteriovenous shunts. Alternatively, it is envisioned that this method can be employed in combination with other gene therapeutic approaches employing the delivery of genetic material in viral or non-viral form. The scope of the present invention also includes diseases that are known to be the consequence of vascular diseases, such as Coronary Heart Disease and Myocardial Infarction.

The method of the present invention is also intended to be used as an in vitro method, for example, an in vitro screening method that allows the identification of genes that are modulated in vascular cells by AP-1 and/or C/EBP or related proteins. Such a method would entail the in vitro contacting of said cells with a composition comprising one or more double-stranded nucleic acid(s) capable of sequence-specifically binding the transcription factor AP-1 and/or C/EBP or related proteins. The transcription level of thousands of genes could then be simultaneously monitored and compared with and without added composition using a DNA-Chip array as described, for instance, in U.S. Pat. No. 5,837,466.

Another aspect of the present invention is a double stranded nucleic acid capable of sequence-specific binding to the transcription factor AP-1 or a related transcription factor having one of the sequences of (SEQ ID 5 or 9 through 20 having the sequences: 5'CTGTTGGTGAC-TAATAACACA 3' (SEQ ID NO: 9) (designed AP-1); 5'CTGTGGGTGACTAATCACACA 3' (SEQ ID NO: 10) (designed AP-1); 5' GTGCTGACTCAGCAC 3' (SEQ ID NO: 11) (designed AP-1); 5'CGCTTAGTGACTAAGCG 3' (SEQ ID NO: 12) (designed AP-1); 5' TGTGCTGACT-CAGCACA 3' (SEQ ID NO: 13) (designed AP-1); 5' TTGT-GCTGACTCAGCACAA 3' (SEQ ID NO: 14) (DESIGNED ap-1); 5'TCGCTTAGTGACTAAGCGA 3' (SEQ ID NO: 15) (designed AP-1); 5' TGCTGACTCATGAGTCAGCA 3' (SEQ ID NO: 16) (designed AP-1); 5' TGCTGACTAATT-AGTCAGCA 3' (SEQ ID NO: 17) (designed AP-1); 5' GTCGCTT AGTGACTAAGCGAC 3' (SEQ ID NO: 18) (designed AP-1); 5' CTTGTGCTGACTC AGCACAAG 3' (SEQ ID NO: 19) (designed AP-1); 5' TTGCTGACTCAT-GAGTCA GCAA 3' (SEQ ID NO: 20) (designed AP-1).

Another aspect of the present invention is a double stranded nucleic acid capable of sequence-specific binding to the transcription factor C/EBP or a related transcription factor having one of the sequences of (SEQ ID 6 or 21 through 30 having the sequences: GCTTGTGCGG-GAATAAATAG 3' (SEQ ID NO: 21) (designed C/EBP); 5'AGGAATA ATGGAATGCCCTG 3' (SEQ ID NO: 22) (designed C/EBP); 5' GACATTGCGCAATGTC 3' (SEQ ID NO: 23) (designed C/EBP); 5'AGCATTGGCCAATGCT 3' (SEQ ID NO: 24) (designed C/EBP); 5' CGACATTGCG-CAATGTCG 3' (SEQ ID NO: 25) (designed C/EBP); 5' AGGCATTGGCCAATGCCT 3' (SEQ ID NO: 26) (designed C/EBP); 5'ACG ACATTGCGCAATGTCGT 3' (SEQ ID NO: 27) (designed C/EBP); 5'TAGGCATTGG CCAATGCCTA 3' (SEQ ID NO: 28) (designed C/EBP); 5' CTGTTGCGCAATTGCGC AACAG 3' (SEQ ID NO: 29) (designed C/EBP); 5' GACTTGCGCAATTGCGCAAGTC 3' (SEQ ID NO: 30) (designed C/EBP).

Double-stranded nucleic acids of the present invention are between 12 and 22 nucleotides in length. The optimal length of a given nucleic acid is selected to optimize binding to the transcription factor and uptake into the cell. Typically, a double-stranded nucleic acid shorter than 12 bp binds only weakly to its target protein while one longer than 22 bp albeit binding avidly is taken up with lower efficiency by the cell. Binding strength can be determined by EMSA while uptake of the double stranded nucleic acids can be analyzed by northern blot (Sambrook et al. (1989) supra), southern blot (Sambrook et al. (1989) supra), PCR (Sambrook et al. (1989) supra), RT-PCR (Sambrook et al. (1989) supra) or DNA chip array (U.S. Pat. No. 5,837,466) techniques. The nucleic acids of the present invention can be stabilized as described above.

A preferred embodiment of the present invention are nucleic acids that contain a palindromic binding site, thereby comprising in a short double-stranded nucleic acid at least two transcription factor binding sites. A double-stranded nucleic acid designed in this way has a higher statistic chance of binding to a AP-1 and/or C/EBP or a related transcription factor. To facilitate the design of a palindromic binding sequence a mismatch in one side of the palindromic core sequence (AP-1: TGAC and C/EBP: GCAA) can be tolerated. Preferentially, the core sequence is placed in the middle of the nucleic acid to allow optimal binding to AP-1 and/or C/EBP or a related transcription factor.

A nucleic acid of the present invention is rapidly internalized into the cell. A sufficient uptake is characterized by modulation of a gene or genes that can be modulated by AP-1 and/or C/EBP or a related transcription factor. The double-stranded nucleic acid of the present invention preferentially modulates transcription of a gene or genes, after about 2 h of contact with the cell, more preferably after about 1 h, after about 30 min, after about 10 min and most preferably after about 2 min. A typical composition employed in such an experiment comprises 10 µmol/l of double-stranded nucleic acid.

The following figures and examples are merely meant to illustrate and not by any way to limit the scope of the invention.

FIG. 1: Effects of (A) endothelium removal, (B,E) Ro 31-8220 (0.1 µmol/l), (C,F) herbimycin A (0.1 µmol/l), and (D) actinomycin D (1 µmol/l) on ppET-1 mRNA abundance in isolated segments of the rabbit carotid arteries (RbCA) or rabbit jugular vein (RbJV) perfused for 6 h at different levels of intraluminal pressure. Representative RT-PCR analyses, comparable findings were obtained in at least four additional experiments with segments from different animals.

Figure 2:
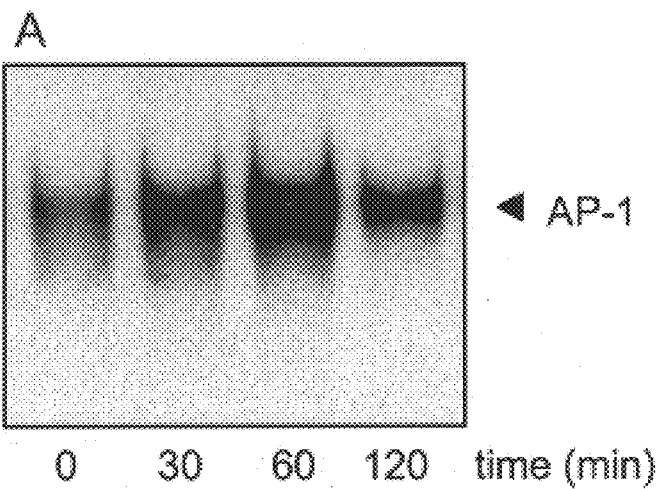
Figure 2:
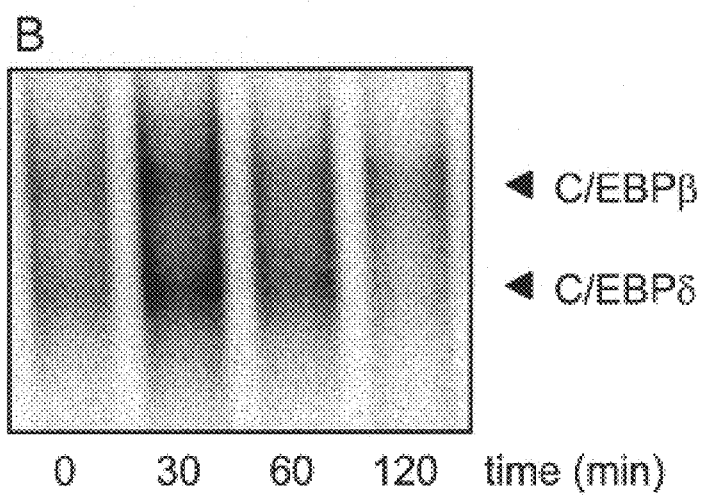

FIG. 2: Time-dependent increase in the nuclear translocation of (A) AP-1 and (B) C/EBP in endothelium-intact segments of the RbJV perfused at 20 mmHg. Representative EMSA, comparable results were obtained in at least two additional experiments.

FIG. 3: Effects of specific Decoy-Oligodesoxynucleotide (dODN) against (B,D) C/EBPmut, (C) GATA-2, and (D) C/EBP on ppET-1 mRNA abundance in endothelium-intact segments of the RbCA or RbJV perfused for 6 h at different levels of intraluminal pressure. (E,F) Effects of (E) Ro 31-8220 (0.1 µmol/l) and (F) herbimycin A (0.9 µmol/l) on ppET-1 mRNA abundance in PAEC (primary culture) incubated under static conditions or stretched for 6 h. Representative RT-PCR analyses, comparable findings were obtained in at least two additional experiments with segments or cells from different animals.

Figure 4:
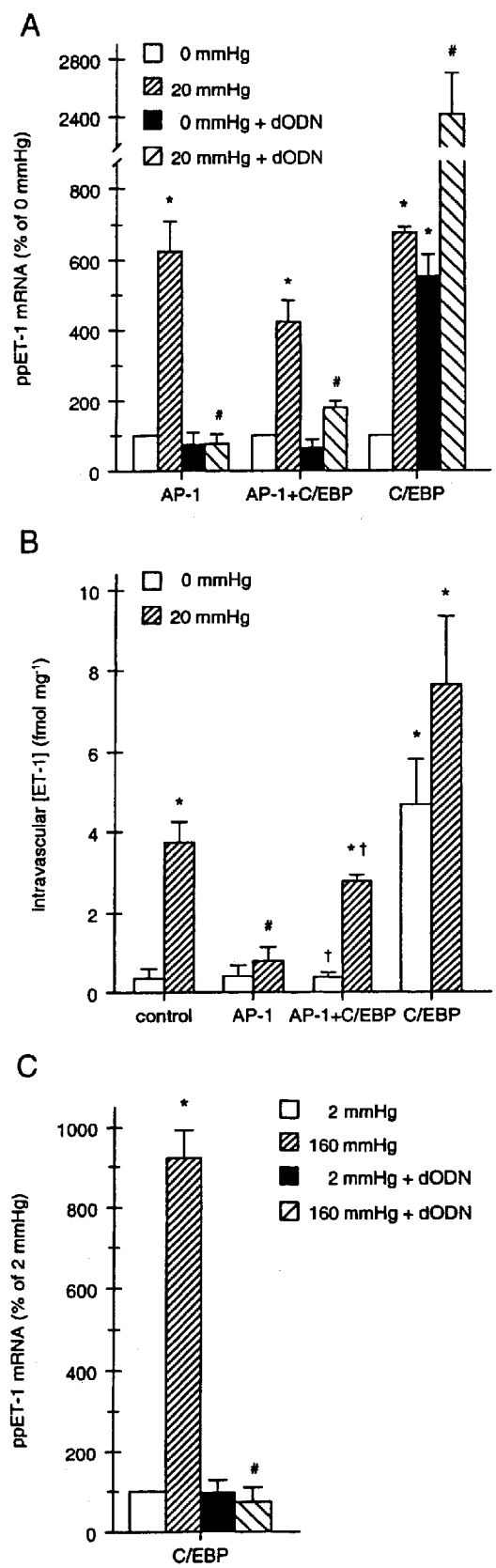

FIG. 4: Effects of specific decoy ODN against AP-1 and C/EBP alone or in combination on (A,C) ppET-1 mRNA abundance (n=3–5) and (B) intravascular ET-1 peptide (n=3) in isolated segments of the RbCA (C) or RbJV (A,B) perfused for 6 h at different levels of intraluminal pressure. *$P<0.05$ vs. 0 or 2 mmHg, #$P<0.05$ vs. 20 or 160 mmHg, †$P<0.05$ vs. 20 mmHg plus C/EBP dODN.

Figure 5:
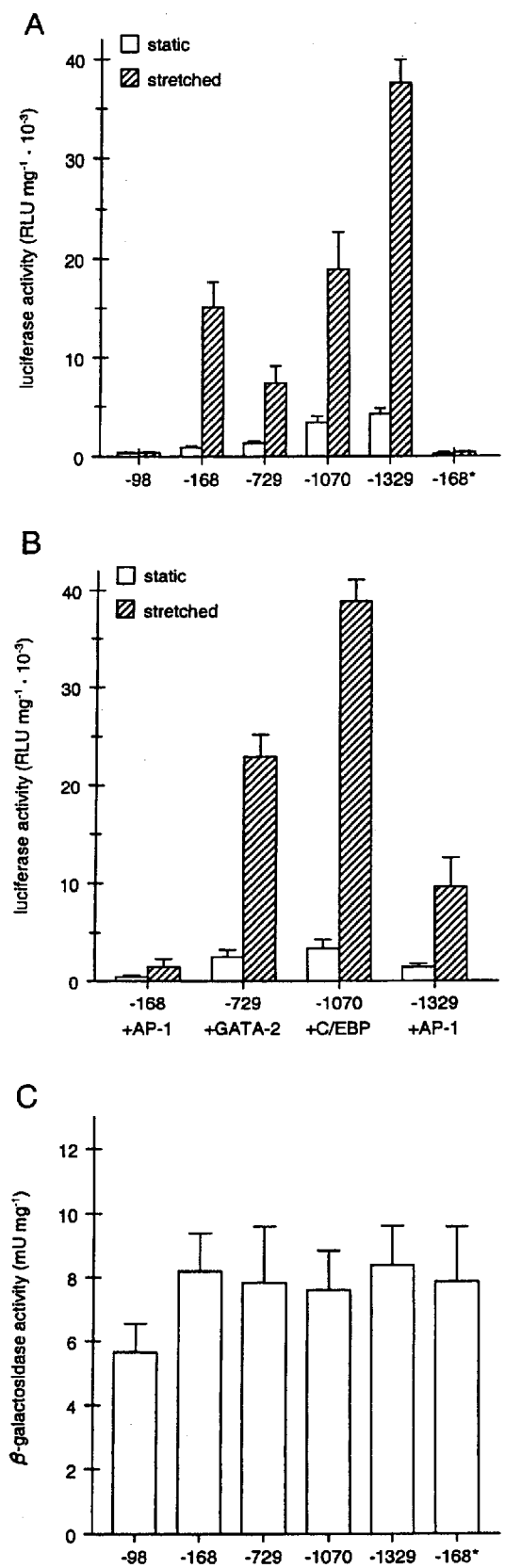

FIG. 5: (A,B) Expression of different rat ppET-1 promoter-luciferase constructs (the asterisk denotes the −168 bp construct without the AP-1 response element ) in cultured PAEC incubated under static conditions or stretched for 6 h in the (A) absence or (B) presence of different dODN (denoted by the plus sign; n=3–7, double determinations). (C) β-Galactosidase activity in cultured PAEC co-transfected with the SV40/β-galactosidase expression vector and different rat ppET-1 promoter-luciferase constructs as an index for the similar transfection efficiency (n=3–7, double determinations).

Figure 6:
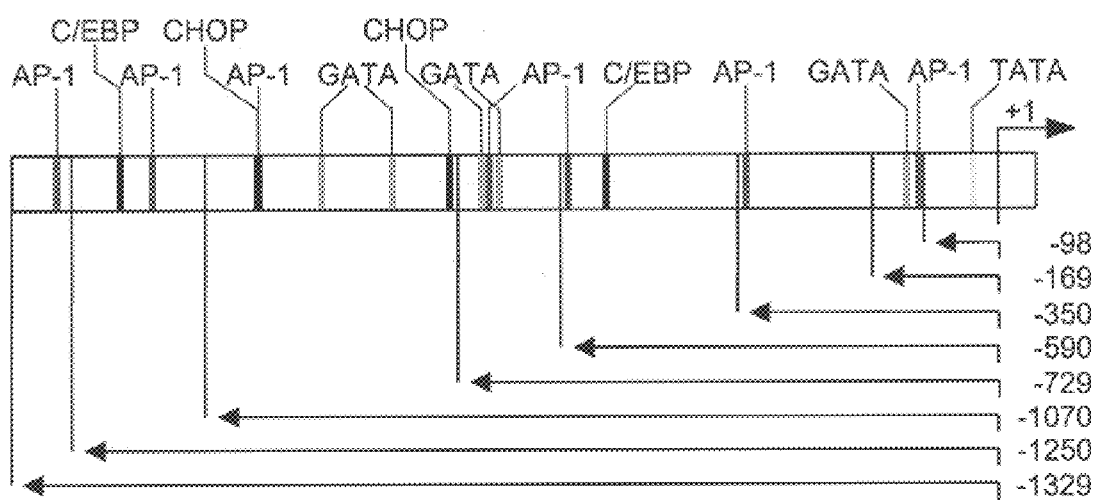

FIG. 6: Scheme of the putative transcription factor binding sites in the promoter of the rat ppET-1 gene indicating in addition the lengths of the various promoter constructs.

Figure 7:
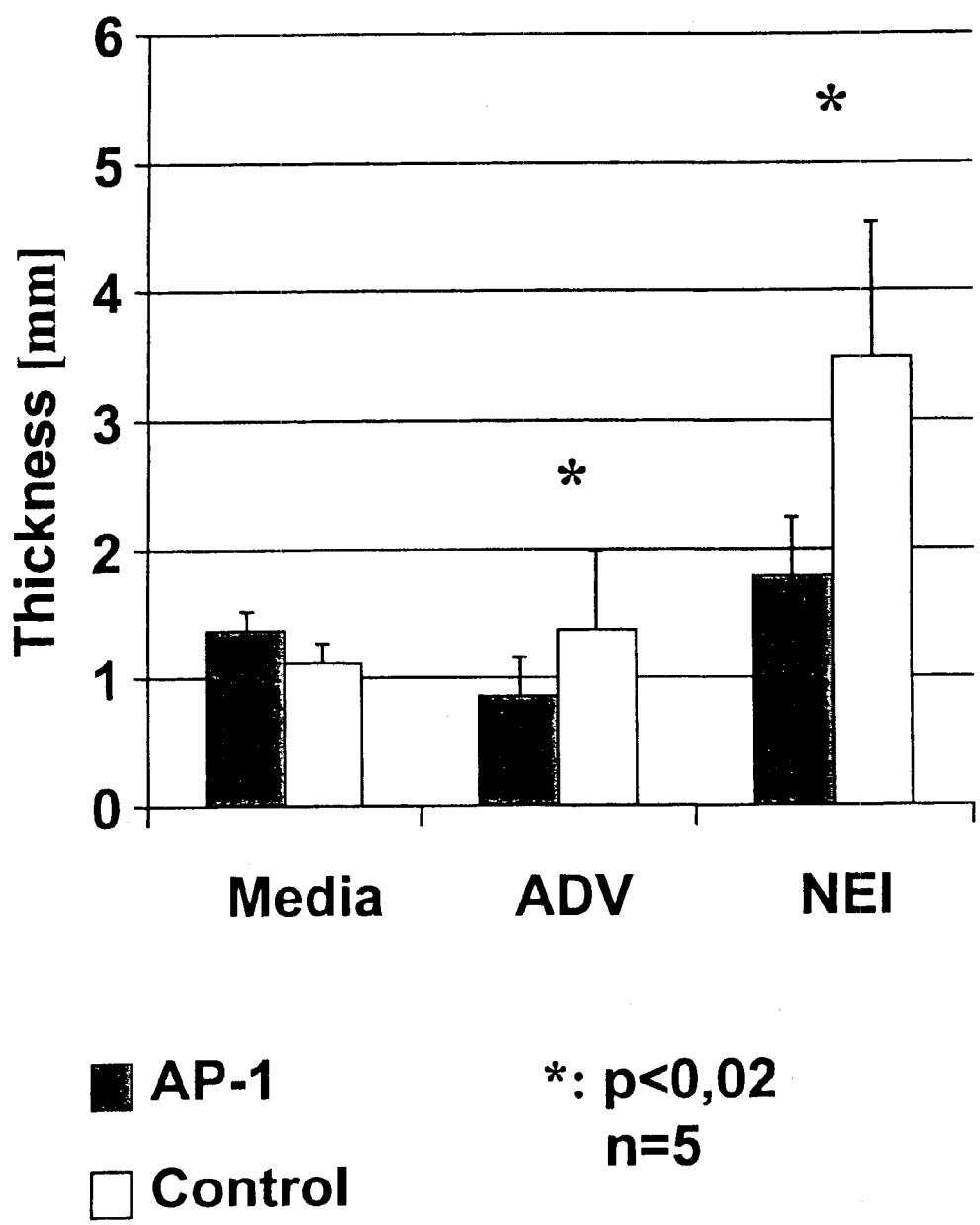

FIG. 7: Diagram of the measurements of the thickness of Mini-pig coronary arteries treated with either AP-1 dODN in saline solution or with saline solution containing no dODN. In the figure ADV stands for adventitia and NEI for neointima.

Figure 8:
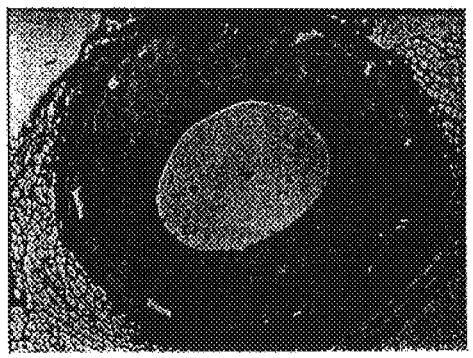
Figure 8:
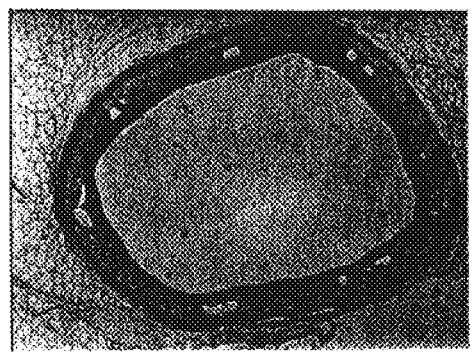

FIG. 8: Photograph of two Mini-pig coronary artery sections that either have been treated with either AP-1 dODN in saline solution or with saline solution containing no dODN.

Figure 9:
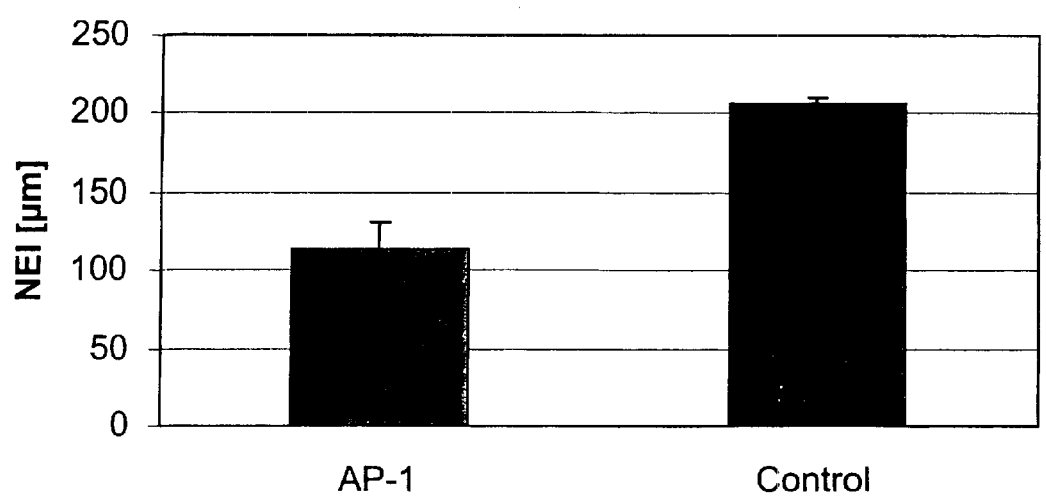

FIG. 9: Diagram of the measurements of the thickness of the neointima (NEI) of rabbit jugular vein segments treated with either AP-1 dODN in saline solution or with saline solution containing no dODN.

EXAMPLES

1. In Situ Model

Male New Zealand White rabbits (2.1±0,1 kg body weight, n=47) were anesthesized with pentobarbitone (60 mg/kg i.v.; Sigma-Aldrich, Deisenhofen, Germany) and exsanguinated. The left and right common carotid arteries (RbCA) were dissected as well as the external jugular vein (RbJV), cleansed of adventitial adipose and connective tissue, and cut into half. The segments were mounted into a specifically designed four-position perfusion chamber where they were stretched back to their in situ length (20.6±0,3 mm) by the aid of moveable cannulae. Their diameter was continuously monitored by video microscopy (Visitron Instruments, Munich, Germany). The lumen of the segments and the surrounding tissue baths were individually perfused (lumen: 1 ml/min; bath 0.5 ml/min) with warmed (37° C.) oxygenated (lumen: 75% $N_2$, 20% $O_2$, 5% $CO_2$, $PO_2$=140 mmHg, $PCO_2$=15–20 mmHg, pH 7.4; bath: 95% $CO_2$, 5% $O_2$, $PO_2$>300 mmHg, $PCO_2$=13–38 mmHg, pH 7.4) Tyrode solution of the following composition: 144.3 mmol/l $Na^+$, 4.0 mmol/l $K^+$, 138.6 mmol/l $Cl^-$, 1.7 mmol/l $Ca^{2+}$, 1.0 mmol/l $Mg^{2+}$, 0.4 mmol/l $HPO_4^{2-}$, 19.9 mmol/l $HCO_3^-$, 10.0 mmol/l D-glucose was used. An IPC roller pump (Ismatec, Wertheim, Germany) was used for perfusion, pumping at a frequency of 1.33 Hz. After a 30-min equilibration period, the segments were perfused at 2, 90 or 160 mmHg for 3–12 h with the aid of an adjustable afterload device system (Hugo Sachs Elektronik, March, Germany).

2. Cell Culture

Endothelial cells were isolated from porcine aortae by treatment with 1 U/ml dispase in Hepes-modified Tyrode solution for 7 min at 37° C., and cultured on gelatin-coated 60 mm culture dishes (2 mg/ml gelatin in 0.1 M HCl for 30 min at ambient temperature) in DMEM/Ham F12 (1:1, v/v) containing 10 U/ml nystatin, 50 U/ml penicillin, 50 µg/ml streptomycin, 5 mmol/l Hepes, 5 mmol/l TES and 20% fetal bovine serum. They were passaged once by using 0.5% Trypsin/0.2%EDTA (w/v), and seeded into BioFlex™ Collagen type I six-well plates (Flexcell, Hillsborough, N.C., USA) that had additionally been coated with gelatin. They were identified by their typical cobblestone morphology, positive immunostaining for von Willebrand factor (vWF) and negative immunostaining for smooth muscle α-actin (Krzesz et al. (1999) 453, 191).

3. RT-PCR Analysis

The frozen segments were minced under liquid nitrogen with the aid of a mortar and a pestle. Total RNA was isolated with the Quiagen RNeasy kit (Quiagen, Hilden, Germany)

followed by cDNA synthesis with a maximum of 3 µg RNA and 200 U Superscript™ II reverse transcriptase (Gibco Life Technologies, Karlsruhe, Germany) in a total volume of 20 µl according to manufacturers instructions. For normalization of cDNA load, 5 µl (around 75 ng cDNA) of the resulting cDNA solution and 20 pmol of each primer (Gibco) were used for elongation factor 1 (EF-1) PCR with 1 U Taq DNA polymerase (Gibco) in a total volume of 50 µl. Elongation factor-1 (EF-1) served as standard for the PCR. PCR products were separated on 1.5% agarose gels containing 0.1% ethidium bromide, and the intensity of the bands was determined densitometrically to adjust cDNA volumes for subsequent PCR analyses by using a CCD-camera system and the One-Dscan Gel analysis software from Scanaltytics (Billerica, Mass., USA).

All PCR reactions were performed individually for each primer pair in a Hybaid OmnE thermocycler (AWG; Heidelberg, Germany). Individual PCR conditions for the cDNA from PAEC were as follows: ppET-1-product size 432 bp, 30 cycles, annealing temperature 53° C., (forward primer) 5' GGAGCTCCAGAAACAGCTGTC 3' (SEQ ID NO: 1), (reverse primer) 5' CTGCTGATAAATACACT-TCTTTCC 3' (SEQ ID NO: 2) (corresponding to nucleotide sequence 233–664 of the rat ppET-1 gene, GenBank accession no. M64711); EF-2-218 bp, 22 cycles, 58° C., 5' GACATCACCAAGGGTGTGCAG 3' (SEQ ID NO: 3), 5' GCGGTCAGCACAATGGCATA 3' (SEQ ID NO: 4) (1990–2207, human EF-2, Z11692).

4. Intravascular ET-1 Concentration

ET-1 was extracted from the weighted segments as described (Hisaki et al. (1994) Am. J. Physiol. 266, 422; Moreau et al. (1997) Circulation 96, 1593), and its concentration determined by using an ELISA kit (Amersham, Freiburg, Germany).

5. Reporter Gene Analysis

Partial sequences of the rat ppET-1 promoter, amplified by PCR, were cloned blunt-end into the Sma-1 restriction site of the multiple cloning region of the luciferase expression vector pCMV TK luc+ after excision of the CMV promoter (Paul et al. (1995) Hypertension 25, 683). The pCMV TK Luc+ construct with and without the CMV promoter served as controls. Site-directed mutagenesis of the AP-1 and GATA site in the −168 bp construct was carried out by using the Transformer™ Site Directed Mutagenesis kit (Clontech, Heidelberg, Germany). Co-transfections for estimation of transfection efficacy were performed with the SV40/β-galactosidase expression vector pUC19 (Paul et al. (1995) supra).

For transfection, 40% confluent porcine aortae endothelial cells were incubated with 1.5 µg plasmid DNA and 15 µl Effectene™ (Qiagen, Hilden, Germany) for 6 h, thereafter the medium was replaced and the cells cultured until they attained 80% confluence (usually after 18–24 h). They were then incubated statically or exposed to 20% cyclic strain at 0.5 Hz in a Flexercell FX-3000 computerized stretch device for 6 h. Luciferase and β-galactosidase activities in the cell lysates were determined by using the corresponding chemiluminescence and photometric assay kits (Promega, Mannheim, Germany), and normalized on the basis of their protein content. Transfection efficiency was estimated at the light microscope level by staining of the cells with the β-galactosidase substrate, o-nitrophenyl-β-D-galactopyranoside (Lim and Cha (1989) Biotechniques 7, 576).

6. Electrophoretic Mobility Shift Analysis (EMSA)

Preparation of nuclear extracts and [32P]-labelled double stranded consensus oligonucleotides (Santa Cruz Biotechnology, Heidelberg, Germany), non-denaturing polyacrylamide gel electrophoresis, autoradiography and supershift analyses were performed as described (Krzesz et al. (1999) supra). Oligo nucleotides with the following single stranded sequence were used (core sequences are underlined): AP-1, 5' CGCTTGA<u>TGACTCA</u>GCCGGAA 3' (SEQ ID NO: 5); C/EBP, 5' TGCAGA<u>TTGCGCAAT</u>CTGCA 3' (SEQ ID NO: 6).

7. Decoy-Oligodeoxynucleotide (dODN) Technique

Double-stranded dODN were prepared from the complementary single-stranded phosphoro-thioate-bonded oligodeoxynucleotides (Eurogentec, Cologne, Germany) as described (Krzesz et al. (1999) supra). The lumen of the carotid artery or jugular vein segments were either filled with medium containing the double-stranded dODN or the dODN were pre-incubated with the cultured PAEC for 4 h at a concentration of 10 µM, conditions that had been optimized before on the basis of EMSA and RT-PCR analyses. Thereafter, the dODN-containing medium was washed out by perfusion (segments) or replaced by fresh medium (PAEC). The single-stranded sequences of the dODN were as follows (underlined letters denote phosphorothioate-bonded bases): AP-1, 5' <u>CGC</u>TTGATGACTCAGCC<u>GGAA</u>3' (SEQ ID NO: 5); C/EBP, 5' <u>TGCA</u>GATTGCGCAATC<u>TGCA</u> 3' (SEQ ID NO: 6); C/EBPmut, 5' <u>TGCA</u>GAGACTAGTCTC<u>TGCA</u> 3' (SEQ ID NO: 7); GATA-2, 5' <u>CAC</u>TTGATAACAGAAAGTGATAA<u>CTCT</u> 3' (SEQ ID NO: 8).

8. Statistical Analysis

Unless indicated otherwise, all data in the figures and text are expressed as mean±SEM of n experiments with segments or cells from different animals. Statistical evaluation was performed by Students t-test for unpaired data with a P value <0.05 considered statistically significant.

9. Pre-pro ET-1 mRNA Expression

Pressurizing of the RbCA to 160 mmHg and that of the RbJV to 20 mmHg resulted in a maximum distension with an average increase in outer diameter of 208 and 274%, respectively. The mRNA level of the house-keeping reference gene, EF-1, was not altered by these changes in perfusion pressure, and no significant loss of EC from the perfused segments could be detected. Raising the perfusion pressure from 2 or 90 to 160 mmHg (RbCA) or from 0 or 5 to 20 mmHg (RbJV) resulted in a marked increase both in ppET-1 mRNA and intravascular ET-1 (FIGS. 1, 3 and 4). This presumably deformation-induced ppET-1 expression was confined to the endothelium, as it was strongly diminished following denudation of the segments (FIG. 1a). Pretreatment of the RbJV with the protein kinase C (PKC) inhibitor (Wilkinson et al. (1993) Biochem. J. 295, 335), Ro 31-8220 (0.1 µmol/l, FIG. 1b), but not with the Src family-specific tyrosine kinase inhibitor (Banes et al. (1995) Biochem. Cell Biol. 73, 349; Birukov et al. (1997) Circ. Res. 81, 895), herbimycin A (0.1 µmol/l, FIG. 1c), strongly inhibited both the basal and pressure-dependent expression of ppET-1. In contrast, Ro 31-8220 was without effect in the RbCA (FIG. 1e) while the deformation-induced increase in ppET-1 expression was virtually abolished following exposure of the segments to herbimycin A (FIG. 1f). Blockade of RNA synthesis with actinomycin D (1 µmol/l) abrogated the pressure-induced increase in ppET-1 mRNA (FIG. 1d) and intravascular ET-1 in both types of vessels.

Result: ET-1 gene is de novo expressed in response to the pressure-dependent deformation of the EC.

10. Transcription Factor Activation

EMSA using AP-1 and C/EBP oligos revealed a transient (i.e., 30–60 min) and significant (two- to threefold) increase in activity upon exposure of the RbJV to an intraluminal pressure of 20 mmHg (n=3–9 for each transcription factor). This nuclear translocation was most prominent and reproducible in the case of AP-1 (FIG. 2a) and C/EBP (FIG. 2b) which according to supershift analyses consisted mainly of the β- and δ-isoform. Moreover, the abundance of AP-1 in the nuclear extracts was strongly reduced both under basal conditions and in the presence of an elevated perfusion pressure following pre-treatment of the RbJV with Ro 31-8220 (from 247±39 to 146±13% of control after 1 h perfusion at 20 mmHg, n=3). Virtually identical results were obtained for AP-1 and C/EBP in the RbCA where in addition the pressure-induced activation of C/EBPβ and δ was blocked by herbimycin A.

Results: AP-1 and C/EBP show increased binding activity in extracts of RbJV and RbCA after an increase in intraluminal pressure.

11. Role of AP-1 and C/EBP

Figure 3A:
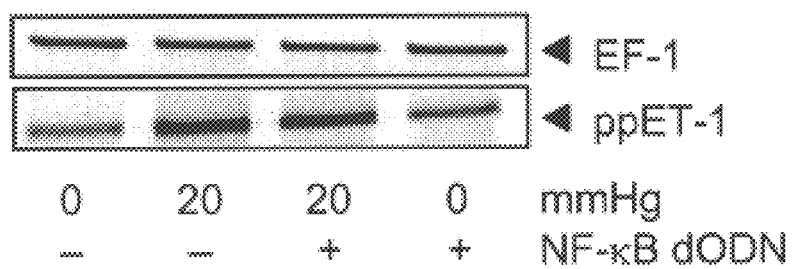
Figure 3A:
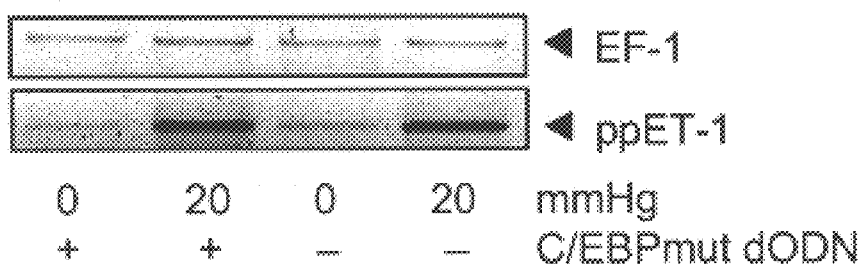
Figure 3A:
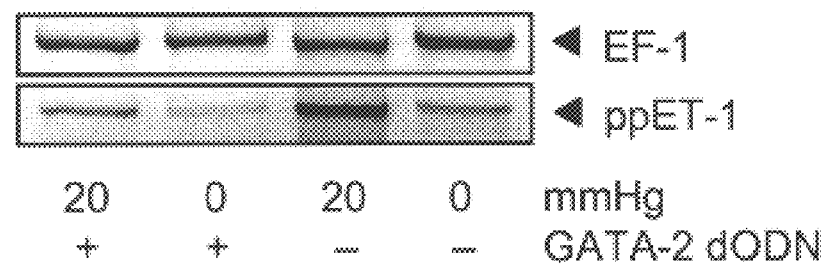
Figure 3B:
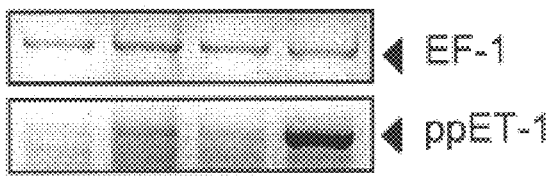
Figure 3B:
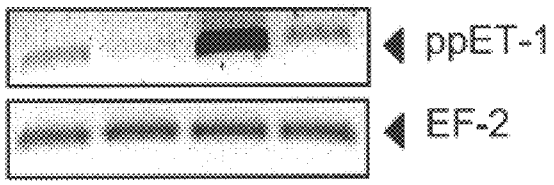
Figure 3B:
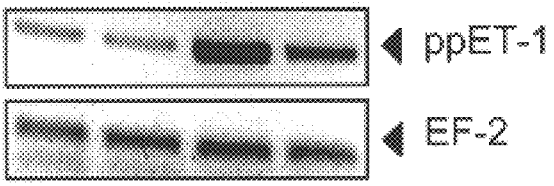

Both the AP-1 and C/EBP dODN displayed prominent, albeit divergent effects. Thus, in RbJV the AP-1 dODN abolished the pressure-dependent but not basal ppET-1 mRNA (FIG. 4a) and ET-1 peptide abundance (FIG. 4b). The C/EBP dODN, on the other hand, markedly enhanced both the basal and pressure-dependent ppET-1 expression to a similar extent (FIGS. 4a and b). In contrast, no such effect was observed with the mutated dODN, C/EBPmut, reinforcing the specificity of the dODN technique (FIG. 3b). Combination of the AP-1 with the C/EBP dODN significantly reversed the potentiating effect of the latter on ppET-1 expression (FIGS. 4a and b).

Unlike in the RbJV, the C/EBP but not the C/EBPmut dODN abolished the pressure-induced increase in ppET-1 expression in the RbCA without affecting the basal level (FIG. 4c). In these segments, the AP-1 dODN modestly attenuated ppET-1 expression in a manner similar to that of the GATA-2 dODN in the RbJV (FIG. 3c).

Result: ppET-1 induction in response to pressure can be inhibited in RbJV by AP-1 dODNs and in RbCA by C/EBP dODNs.

12. Stretch Response of the Rat ppET-1 Promoter

PAEC were transiently transfected with different rat ppET-1 promoter-luciferase constructs. These cells were chosen, as they express much higher levels of both ppET-1 mRNA and ET-1 peptide in response to cyclic strain, an effect that is attenuated both by Ro 31-8220 (FIG. 3e) and herbimycin A (FIG. 3f). According to β-galactosidase staining and measurements of β-galactosidase activity, transfection efficacy was estimated to be approximately 15%. All transfected promoter constructs (−98, −168, −350, −590, −729, −1070, −1250 and −1329 bp) were expressed by the PAEC under static conditions, albeit to a different degree, and apart from the −98 bp construct revealed a marked increase in luciferase activity when exposed to cyclic strain for 6 h (FIG. 5a). The distinct differences in luciferase activity between individual promoter constructs were not due to differences in β-galactosidase transfection efficacy, as the activity of the enzyme in the double transfected cells appeared to be rather uniform (FIG. 5c).

The full length promoter construct displayed the highest activity in stretched PAEC (approximately 40% of the luciferase activity of the CMV-driven gene under static conditions). The shortest stretch-responsive construct was the −168 bp fragment, the expression level of which was about half of that of the full length promoter construct (FIGS. 5a and b). Deletion of the single AP-1 binding site at −110 bp to −100 bp abrogated the stretch responsiveness (FIG. 5a). A similar effect was obtained when PAEC transfected with this construct were pretreated with the AP-1 dODN (63 and 93% inhibition, respectively; FIG. 5b) or with 0.1 μmol/l Ro 31-8220 to block the activity of PKC (abolition of basal and decrease in stretch-induced luciferase activity by 84%). In contrast, a GATA-2 consensus dODN reduced basal and stretch-induced luciferase activity in PAEC transfected with the −168 bp construct only by 28 and 31%, respectively. Moreover, both basal and stimulated expression of the full length promoter construct were clearly inhibited (by 58 and 74%, respectively) after exposure to the AP-1 dODN (FIGS. 5a and b).

The C/EBP dODN had no significant effect on luciferase activity in PAEC transfected with the −590, −729 or −1250 bp constructs, but significantly enhanced the stretch-dependent luciferase activity in PAEC transfected with the −1070 bp construct (FIG. 5b).

Result: Stretch responsiveness of the ppET-1 promoter in PAECs depends on AP-1. ppET-1 promoter activation can be inhibited by AP-1 dODN but not by C/EBP dODN.

13. Prevention of In-stent Proliferation in Pig Coronary Arteries

Mini-pigs (Göttingen strain, 44–55 kg) were sedated by intramuscular injection of azaperone, intubated and anaesthetized ($O_2/N_2O$). Supplementary doses of ketamine and morphine were administered intravenously as required. Animals were anticoagulated intravenously with liquemine (100 I.U./kg body weight) and acetylsalicylic acid (250 mg). Surgery was performed under sterile conditions as follows: The left or right carotid artery was surgically exposed and a guiding catheter was installed to cannulate the left or right coronary artery. Angiograms of the coronary arteries were performed and optionally nitroglycerin was injected for prevention of coronary spasm. After subsequent ballooning (3.0 mm, inflation pressure 12 atm) of the coronary arteries (RCX or LAD), a Dispatch catheter (3.0 mm) was placed for infusion of the AP-1 decoy-ODN (20 nmol in 10 ml saline in one coronary artery or that of a control solution (Tris-HCl/EDTA buffer (10 mmol/l mmol) diluted in saline) in the other coronary artery over 20 min with an inflation pressure of 6 atm followed by implantation of an ACS Multilink stent (8 mm) into both coronary arteries. Wounds were closed and four weeks after surgery animals were sacrificed to harvest the coronary arteries.

To determine the effect of the AP-1 decoy-ODN, morphometric analysis was performed on methylacrylate-embedded hematoxylin/eosin-stained sections of the perfusion-fixed (4% buffered formaldehyde at 100 mmHg) coronary artery segments. The quantitative results are depicted in FIG. 7. Treatment of coronary arteries with the AP-1 decoy-ODN resulted in a marked decrease in neointimal and adventitial thickness, i.e: media AP-1 1.38 mm, control 1.12 mm; adventitia (ADV): AP-1 0.85 mm, control 1.38 mm; neointima (NEI): AP-1 1.78 mm, control 3.49 mm. The surface area of the lumen was 4.6 $mm^2$ for AP dODN treated coronary arteries and 3.17 $mm^2$ for the control arteries. Thus treatment with dODN led to a reduction of neointimal thickness of approximately 50% and a reduction of adventitial thickness of approximately 40%. Consequently, inhibition of neointimal and adventitial proliferation resulted in an increase in surface area of the lumen of approximately 45% in the AP-1 decoy-ODN-treated coronary arteries as compared to control vessels. The effect is illustrated by photographs of thin sections of AP-1 treated and control vessels (FIG. 8).

Result: Treatment with AP-1 dODN prior to implantation of a stent dramatically reduces proliferation of Mini-pig coronary artery cells and thus leads to an increased coronary artery lumen surface area post surgery.

14. Transfection of Interposition Vein Grafts in Rabbits

Rabbits (New Zealand White, 3–4 kg) were sedated by intramuscular injection of azaperone, intubated and anaesthetized ($O_2/N_2O$). Supplementary doses of ketamine and morphine were administered intravenously as required. Animals were anticoagulated intravenously with liquemine (100 I.U./kg body weight) and acetylsalicylic acid (100 mg). Surgery was performed under sterile conditions as follows: Over a length of 3 cm the left or right carotid artery was surgically exposed and a segment of the adjacent jugular vein of approximately 2 cm was excised. Following ex vivo transfection by perfusion with AP-1 decoy-ODN (20 µM for 30 min at 37° C.) or a control solution (TE buffer diluted in saline) the vein segment was connected to the carotid artery by end-to-side anastomosis. Wounds were closed and four weeks after surgery animals were sacrificed to harvest the jugular vein segments.

To determine the effect of the AP-1 decoy-ODN, morphometric analysis was performed on OCT-embedded van Gieson-stained sections of the perfusion-fixed (4% buffered formaldehyde at 80 mmHg) jugular vein segments. The results are depicted in FIG. 9. Treatment of jugular vein segments with the AP-1 decoy-ODN resulted in a marked decrease in neointimal thickness, i.e: AP-1 113.9 $\mu m^+/-16.3$, control 206.8 $\mu m^+/-4$. Thus treatment with dODN led to a reduction of neointimal thickness of approximately 45%. Consequently, inhibition of neointimal proliferation led to an increase in surface area of the lumen in the AP-1 decoy-ODN-treated jugular vein segments as compared to control vessels.

Result: Treatment of a jugular vein segment with AP-1 dODN prior to implantation as interposition vein graft dramatically reduces proliferation of the jugular vein cells and thus leads to an increased jugular vein lumen area post surgery.

15. Transfection of Injured Carotid Arteries to Inhibit Restenosis

To characterize the effect of C/EBP decoy on neointimal lesion formation in carotid arteries of the rabbit after PTA the establishment of an in vivo model of restenosis and atherosclerosis is envisioned.

Adult New Zealand White rabbits (3–4 kg) are used. Some animals are fed a diet containing 1% cholesterol for 2 weeks prior to balloon injury, and they are maintained on that diet until harvest of transfected vessels. Balloon injury is carried out after induction of anesthesia as described under 13. Following a vertical neck incision, the right common carotid artery dissected free of surrounding tissue and side branches are ligated. Rabbits will be systemically heparinized by intravenous injection of heparin (100 U/kg) prior to clamping the carotid artery. A 2 French Fogarty embolectomy catheter is introduced through a branch of the external carotid artery and inflated in the middle portion of the common carotid artery and then pulled back to the bifurcation. This procedure is repeated three times resulting in complete endothelial denudation. Then, an infusion catheter filled with normal saline is advanced into the artery to flush the carotid artery. After achieving proximal control, the decoy solution is infused and incubated for 30 min dwell time. Blood flow through the common carotid artery is re-established after the ligation of the side branch used for introduction of the catheter, hemostasis established, and the wound is closed.

At time intervals described above, the rabbits are anesthetized again and the vessel segments harvested. Experiments subjected to the efficiency study of the dODN treatment are anesthetized again and the vessel segments harvested. Experiments subjected to the efficiency study are terminated after 2 days, EMSA is performed to demonstrate efficient "decoying" of the targeted transcription factor (C/EBP). The biologic effect of decoy treatment is demonstrated at 4 weeks after transfection by standard computerized morphometry.

What is claimed is:

1. A method of modulating the transcription of at least one gene in a vascular cell, the method comprising:

locally administering to a vascular cell a composition comprising one or more double stranded nucleic acid(s), in a non-viral form, wherein said nucleic acid(s) exhibits sequence specific binding to an AP-1 family transcription factor, wherein said binding results in reduction of proliferation of said vascular cell.

2. A method according to claim 1, wherein said vascular cell is part of a vessel or vascular graft.

3. A method according to claim 2, wherein said vascular graft is contacted in vivo or ex vivo with said composition.

4. A method of modulating the transcription of at least one gene in a vascular cell, the method comprising:

locally administering to a vascular cell a composition comprising one or more double stranded nucleic acid(s), in a non-viral form, wherein said nucleic acid(s) exhibits sequence specific binding to a C/EBP family transcription factor, wherein said binding results in reduction of proliferation of said vascular cell.

5. A method according to claim 4, wherein said vascular cell is a smooth muscle cell (SMC) or endothelial cell.

6. A method according to claim 5, wherein said cell is part of a vessel or vascular graft.

7. A method according to claim 6, wherein said vessel is a coronary or peripheral artery or a vein.

8. A method of modulating the transcription of at least one gene in a vascular cell, the method comprising:

locally administering to a vascular cell a composition comprising double stranded nucleic acids, in a non-viral form, wherein said nucleic acids exhibit sequence specific binding to an AP-1 family transcription factor and a C/EBP family transcription factor, wherein said binding results in reduction of proliferation of said vascular cell.

9. A method according to claim 8, wherein said vascular cell is a smooth muscle cell (SMC) or endothelial cell.

10. A method according to claim 9, wherein said cell is part of a vessel or vascular graft.

11. A method according to claim 10, wherein said vessel is a coronary or peripheral artery or vein.

12. A method according to claims 1 or 4, wherein the gene or genes regulate(s) proliferation or migration of said cells.

13. A method according to claims 1 or 4, wherein said gene is selected from the group consisting of an endothelin gene, a macrophage chemotactic protein (MCP) gene, a nitric oxide synthase (NOS) gene, the E-selectin gene, the intercellular adhesion molecule-1 (ICAM-1) gene, the interleukin-8 (Il-8) gene, or the interleukin-6 (Il-6) gene.

14. A method according to claim 13, wherein said endothelin gene is the preproendothelin-1 gene or the endothelin receptor B gene, said MCP gene is the MCP-1 gene and said NOS gene is the inducible NOS gene.

15. A method according to claims 1 or 4, wherein modulating of transcription leads to activation of said gene or genes.

16. A method according to claims 1 or 4, wherein modulating of transcription leads to loss of activation or repression of said gene or genes.

17. A method according to claims 1 or 4, wherein the double-stranded nucleic acid comprises one or more copies of a sequence that specifically binds the transcription factor AP-1 or C/EBP.

18. A method according to claims 1 or 4, wherein said double-stranded nucleic acid is an oligonucleotide.

19. A method according to claim 18, wherein said oligonucleotide is stabilized.

20. A method according to claim 19, wherein said oligonucleotide is stabilized by comprising modified internucleotide phosphate residues, dephospho bridges, or modified internucleotide phosphate residues and dephospho bridges.

21. A method according to claim 20, wherein said modified internucleotide phosphate residues are selected from the group consisting of methylphosphonate, phosphorothioate, phosphor-amidates and phosphate esters.

22. A method according to claim 20, wherein said dephospho bridges are selected from the group consisting of siloxane bridges, carbonate bridges, carboxymethyl ester bridges, acetamidate bridges and thioether bridges.

23. A method according to claim 19, wherein said oligonucleotide is stabilized by comprising structural features that increase the half life of said oligonucleotide.

24. A method according to claim 23, wherein said structural features are selected from the group consisting of hairpins and dumbbells.

25. A method according to claim 18, wherein said oligonucleotide has a length between 10 and 100 bp.

26. A method according to claim 25, wherein said oligonucleotide has a length between 20 and 60 bp.

27. A method according to claims 1 or 4, wherein said composition further comprises at least one buffer.

28. A method according to claims 1 or 4, wherein said composition further comprises one or more suitable additives or auxiliaries.

29. A method of treating vascular diseases, the method comprising:

locally administering a composition comprising one or more double stranded nucleic acid(s), in a non-viral form, wherein said nucleic acid(s) exhibits sequence specific binding to an AP-1 family transcription factor, to vascular cells in an amount sufficient to modulate the transcription of at least one gene in said vascular cells, wherein said modulation of transcription results in the reduction of proliferation of said vascular cells, wherein the reduction of proliferation results in the treatment of vascular disease.

30. A method according to claim 29, wherein said vascular disease is selected from the group consisting of a vascular proliferative disorder, restenosis, intimal hyperplasia of arterial or venous bypass grafts, and graft vasculopathy or hypertrophy.

31. A method of treating vascular diseases, the method comprising:

locally administering a composition comprising one or more double stranded nucleic acid(s), in a non-viral form, wherein said nucleic acid(s) exhibits sequence specific binding to an C/EBP family transcription factor, to vascular cells in an amount sufficient to modulate the transcription of at least one gene in said vascular cells, wherein said modulation of transcription results in the reduction of proliferation of said vascular cells, wherein the reduction of proliferation results in the treatment of vascular disease.

32. The method according to claim 31, wherein said vascular disease is selected from the group consisting of a vascular proliferative disorder, restenosis, intimal hyperplasia of arterial or venous bypass grafts, and graft vasculopathy or hypertrophy.

33. A method of treating a condition that is a consequence of a vascular disease, the method comprising:

locally administering a composition comprising one or more double stranded nucleic acid(s), in a non-viral form, wherein said nucleic acid(s) exhibits sequence specific binding to an AP-1 family transcription factor, to vascular cells in an amount sufficient to modulate the transcription of at least one gene in said vascular cells, wherein said modulation of transcription results in the reduction of proliferation of said vascular cells, wherein the reduction of proliferation of said vascular cells results in the treatment of a condition that is a consequence of a vascular disease.

34. A method of treating a condition according to claim 33, wherein said condition is a coronary heart disease or myocardial infarction.

35. A method of treating a condition according to claim 29 or 33, wherein said method is used as an adjuvant therapy for a treatment used in vascular disease.

36. A method of treating a condition according to claim 35, wherein said treatment used in said vascular disease is selected from the group consisting of PTCA, PTA, bypass operations, and application of arterio-venous shunts.

37. A method of treating a condition that is a consequence of a vascular disease, the method comprising:

locally administering a composition comprising one or more double stranded nucleic acid(s), in a non-viral form, wherein said nucleic acid(s) exhibits sequence specific binding to an C/EBP family transcription factor, to vascular cells in an amount sufficient to modulate the transcription of at least one gene in said vascular cells, wherein said modulation of transcription results in the reduction of proliferation of said vascular cells, wherein the reduction of proliferation of said vascular cells results in the treatment of a condition that is a consequence of a vascular disease.

38. The method of treating a condition according to claim 37, wherein said condition is a coronary heart disease or myocardial infarction.

39. The method of treating a condition according to claim 31 or 37, wherein said method is used as an adjuvant therapy for treatment used in vascular disease.

40. The method of treating a condition according to claim 39, wherein said treatment used in said vascular disease is selected from the group consisting of PTCA, PTA, bypass operations, and applications of arterio-venous shunts.

41. A double stranded nucleic acid having the sequence of SEQ ID NO: 11, which is capable of sequence specific binding to an AP-1 family transcription factor.

42. The double stranded nucleic acid according to claim 41, wherein said double stranded nucleic acid is 12 to 22 nucleotides in length.

* * * * *

UNITED STATES PATENT AND TRADEMARK OFFICE
CERTIFICATE OF CORRECTION

PATENT NO. : 6,599,741 B1
DATED : July 29, 2003
INVENTOR(S) : Hecker et al.

It is certified that error appears in the above-identified patent and that said Letters Patent is hereby corrected as shown below:

Title page,
Item [56], References Cited, FOREIGN PATENT DOCUMENTS, replace "DE 2991610 U1" with -- DE 29916160 U1 --; and replace "WO 0 733 370 A1" with -- EP 0 733 370 A1 --.

Column 1,
Line 47, replace "where" with -- were --; and
Line 62, replace "stimuli" with -- stimuli, --

Column 2,
Line 42, replace "c-fos" with -- c-Fos --; and
Line 44, replace "AP-I" with -- AP-1 --.

Column 4,
Line 9, insert -- , -- after "tissue"; and
Line 64, insert -- , -- after "particular".

Column 6,
Line 13, replace "nuclei" with -- nucleic --.

Column 8,
Line 35, replace "peptid-DNA" with -- peptide-DNA --.

Column 9,
Line 34, replace "acid-aptamer" with -- acid aptamer --; and
Line 44, replace "polyethylenimin" with -- polyethylenimine --.

Signed and Sealed this

Twenty-eighth Day of June, 2005

JON W. DUDAS
*Director of the United States Patent and Trademark Office*